(12) United States Patent
Lau et al.

(10) Patent No.: US 11,324,442 B1
(45) Date of Patent: May 10, 2022

(54) BROADBAND IMPEDANCE SPECTROSCOPY AND ITS USE FOR TISSUE WELDING

(71) Applicant: Maquet Cardiovascular LLC, Wayne, NJ (US)

(72) Inventors: Liming Lau, Mountain View, CA (US); Robert M. Pearson, San Jose, CA (US); David Warden, Belmont, CA (US); Ruzbeh Shariff, Belmont, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 506 days.

(21) Appl. No.: 15/361,369

(22) Filed: Nov. 25, 2016

Related U.S. Application Data

(60) Provisional application No. 62/260,226, filed on Nov. 25, 2015.

(51) Int. Cl.
*A61B 18/14* (2006.01)
*A61B 5/00* (2006.01)
(Continued)

(52) U.S. Cl.
CPC ............ *A61B 5/4836* (2013.01); *A61B 5/053* (2013.01); *A61B 5/7225* (2013.01);
(Continued)

(58) Field of Classification Search
CPC .................. A61B 5/4836; A61B 5/053; A61B 2018/00642; A61B 2018/00636;
(Continued)

(56) References Cited

U.S. PATENT DOCUMENTS 4,200,104 A 4/1980 Harris
5,334,193 A 8/1994 Nardella
(Continued)

FOREIGN PATENT DOCUMENTS

DE 3904558 A1 8/1990
EP 0237795 A2 9/1987
(Continued)

OTHER PUBLICATIONS

Pedro Bertemes Filho, "Tissue characterization using an impedance spectroscopy probe"—Doctoral thesis, Dept. of Medical Physics and Clinical Engineering, Univ. of Sheffield, Published Sep. 2002.
(Continued)

*Primary Examiner* — Eun Hwa Kim
*Assistant Examiner* — Adam Z Minchella
(74) *Attorney, Agent, or Firm* — Kevin T. Godlewski

(57) ABSTRACT

A biological tissue monitoring system has control circuitry programmed or configured to monitor an impedance of biological tissue. The control circuitry is programmed or configured to receive or determine an impedance measurement of the biological tissue in response to power delivered to the biological tissue at a plurality of frequencies and a plurality of time points, and adjust or cause to be adjusted the power delivered to the biological tissue at a subsequent time point based on the impedance measurement at the plurality of frequencies and the plurality of time points.

21 Claims, 14 Drawing Sheets

(51) Int. Cl.
*A61B 5/053* (2021.01)
*A61B 18/00* (2006.01)
*A61B 18/12* (2006.01)

(52) U.S. Cl.
CPC ...... *A61B 18/1442* (2013.01); *A61B 18/1492* (2013.01); *A61B 2018/0063* (2013.01); *A61B 2018/00357* (2013.01); *A61B 2018/00363* (2013.01); *A61B 2018/00577* (2013.01); *A61B 2018/00642* (2013.01); *A61B 2018/00702* (2013.01); *A61B 2018/00875* (2013.01); *A61B 2018/126* (2013.01)

(58) Field of Classification Search
CPC ........... A61B 2018/00684; A61B 2018/00875; A61B 2018/00702; A61B 5/7225; A61B 18/1442; A61B 18/1492; A61B 2018/00357; A61B 2018/00363; A61B 2018/00577; A61B 2018/0063; A61B 2018/126

See application file for complete search history.

(56) References Cited

U.S. PATENT DOCUMENTS

| | | | |
|---|---|---|---|
| 5,372,596 A | 12/1994 | Klicek et al. | |
| 2002/0068931 A1 | 6/2002 | Wong et al. | |
| 2002/0077627 A1* | 6/2002 | Johnson | A61B 18/1477 606/41 |
| 2003/0130711 A1* | 7/2003 | Pearson | A61B 18/1477 607/101 |
| 2004/0082946 A1* | 4/2004 | Malis | A61B 18/1206 606/34 |
| 2005/0203504 A1* | 9/2005 | Wham | A61B 18/1206 606/34 |
| 2007/0173811 A1 | 7/2007 | Couture et al. | |
| 2008/0262489 A1 | 10/2008 | Steinke | |
| 2010/0179411 A1* | 7/2010 | Holmstrom | A61B 5/0464 600/374 |
| 2010/0179538 A1* | 7/2010 | Podhajsky | A61B 18/1206 606/35 |
| 2010/0225303 A1* | 9/2010 | Min | A61B 5/053 324/76.24 |
| 2010/0324548 A1* | 12/2010 | Godara | A61B 18/1492 606/34 |
| 2011/0098695 A1* | 4/2011 | Brannan | A61B 18/1815 606/33 |
| 2012/0197243 A1* | 8/2012 | Sherman | A61B 18/02 606/21 |
| 2016/0310203 A1* | 10/2016 | Gaspredes | A61B 18/1445 |

FOREIGN PATENT DOCUMENTS

| | | |
|---|---|---|
| WO | 94/10922 A1 | 5/1994 |
| WO | 95/25472 A1 | 9/1995 |
| WO | 96/38094 A1 | 12/1996 |

OTHER PUBLICATIONS

Casas O, et al. "In vivo and in situ ischemic tissue characterization using electrical impedance spectroscopy" Annals of the NY Academy of Sciences—May 1999 vol. 873: pp. 51-58.

Salazar Y, et al. "Transmural versus nontransmural in situ electrical impedance spectrum for healthy, ischemic, and healed myocardium", IEEE Transactions on Biomedical Engineering—Aug. 2004—vol. 51—No. 8: pp. 1421-1427.

Trebbels D. "Broadband measurement techniques for impedance spectroscopy and time domain reflectometry applications". Göttingen: Cuvillier, 2013.

Trebbels D, et al. "Real-time cannula navigation in biological tissue with high temporal and spatial resolution based on impedance spectroscopy", Conf Proc IEEE Eng Med Biol Soc. (Aug. 31-Sep. 4, 2010): pp. 1886-1889.

Trebbels D, et al. "Capacitive on-line hematocrit sensor design based on impedance spectroscopy for use in hemodialysis machines", Conf Proc IEEE Eng Med Biol Soc. (Sep. 2-6, 2009): pp. 1208-1211.

Trebbels D, et al. "Miniaturized FPGA-based high-resolution time-domain reflectometer." IEEE Transactions on Instrumentation and Measurement—Jul. 2013—vol. 62—No. 7—pp. 2101-2113.

Trebbels D, et al. "High precision phase measurement technique for cell impedance spectroscopy" Journal of Physics Conference Series (2010) vol. 224—pp. 1-4.

Min M, et al. "Broadband spectroscopy of dynamic impedances with short chirp pulses", Physiological Measurement—Jun. 7, 2011—vol. 32: pp. 945-958.

Trebbels D, et al. Online tissue discrimination for transcutaneous needle guidance applications using broadband impedance spectroscopy. IEEE Transactions on Biomedical Engineering—Feb. 2012; vol. 59—No. 2: pp. 494-503.

Paavle T, et al. "Low-energy chirps for bioimpedance measurement", TSP 2011; (2011): pp. 398-402.

Latimer, Cassandra A. et al, "Effect, of collagen and elastin content on the burst pressure of human blood vessel seals formed with a bipolar tissue sealing system", Journal of Surgical Research, vol. 186 (2014), pp. 73-80.

Cotter, N.E. et al, "Laboratory Project 3—Model of Tissue Impedance" pp. 1-6—Retrieved Oct. 23, 2017.

Bass, Lawrence S. et al, "Laser Tissue Welding: A Comprehensive Review of Current and Future Clinical Applications", Lasers in Surgery and Medicine, vol. 17 (1995), pp. 315-349.

Appendix A—Brief Introduction to bioimpedance—pp. 411 to 422—Univ. College London. (htttps://www.ucl.ac.uk/medphys/research/eit)—Retrieved Apr. 21, 2014.

* cited by examiner

| | | |
|---|---|---|
| A. | Start of power delivery | Initial tissue state. Cell membranes are intact. | Capacitive contribution of intact cell membranes results in higher Zreal values at lower frequencies (conduction through interstitial fluid only) compared with at higher frequencies (conduction through interstitial and cytoplasmic fluids). |
| B. | Zreal decreases and Zimag increases from initial values | Tissue heating and cell membrane rupture begin. | Overall values of Zreal decrease as tissue temperature increases. Zreal values at lower frequencies decrease as cell membranes rupture, thus reducing their capacitive effect (conduction through released cytoplasm). |
| C. | Minimum values of Zreal are reached | Tissue heating continues. Cell membrane rupture is substantially complete. Limited amount of tissue desiccation occurs. *Weld formation (collagen and elastin bonding) begins under a combination of elevated temperature, applied pressure, and high moisture content/molecular mobility.* | No further decrease in low frequency measurements of Zreal, as cell membrane rupture is substantially complete. Minimum Zreal values are reached, as combination of cytoplasmic and interstitial fluids (unimpeded by intact cell membranes) increases overall electrical conductivity. Increased temperatures further enhance this effect. Tissue moisture content is near its peak, as evidenced by the minimum values of Zreal. Water in the tissue absorbs energy (specific heat capacity) but remains predominantly in liquid phase. |
| D. | Dwell at/near minimum Zreal, occurrence of minimum range of Zreal | Tissue heating continues. Limited amount of tissue desiccation occurs. *Majority of weld formation (collagen and elastin bonding) occurs during this stage due to conditions of high temperature, applied pressure, and high molecular mobility for a substantial period of time.* | Moisture content remains near its peak, in liquid phase, with minimal loss through vaporization, as evidenced by minimal change (increase) in impedance values. The water continues to absorb energy, increasing in temperature. |
| E. | Values of Zreal begin to increase | Substantial tissue desiccation begins. *Molecular mobility decreases with increasing desiccation.* | Water vaporization and subsequent exit from tissue reduces tissue moisture content, as evidenced by the start of pronounced changes in tissue impedance. |
| F. | Maximum values of Zimag are reached | | |
| G. | Zreal rapidly increases | Tissue desiccation is nearly complete. *Welds are "set" as molecular mobility is greatly decreased in the dry tissue.* | Rapidly increasing Zreal and decreasing Zimag indicate a rapid rate of decrease in tissue water content, as electrically-conductive water quickly exits the tissue as vapor. |
| H. | Zreal rate of increase slows | Tissue desiccation is complete. *Welded tissue is at its initial bond strength (barring thermal damage or rehydration effects).* | Tissue desiccation is complete, as evidenced by high values of Zreal, low values of Zimag, and slowing in the rate of change of impedance. Impedance values at this stage reflect the electrical properties of the dry tissue (e.g., high Zreal due to low electrical conductivity of desiccated tissue). |

FIG. 3

BROADBAND IMPEDANCE SPECTROSCOPY AND ITS USE FOR TISSUE WELDING

CROSS REFERENCE TO RELATED APPLICATIONS

This application claims priority to U.S. Provisional Patent Application No. 62/260,226, filed Nov. 25, 2015, the entire content of which is incorporated herein by reference.

TECHNICAL FIELD

The present disclosure relates to biological tissue monitoring and, in some aspects, to using broadband impedance spectroscopy to monitor an impedance of biological tissue in connection with tissue welding, and optionally to adjust power delivered to the biological tissue during welding and/or determine a condition and weld stage of the tissue.

BACKGROUND

Hyperthermic welding of biological tissue has been practiced for decades, by applying a combination of heat and pressure to the target to be sealed. The mechanism of action is believed to comprise tissue denaturation, in particular, of its collagen and elastin components, followed by intermolecular entanglement and/or chemical bonding to fuse (e.g., weld) adjacent structures. This concept is frequently utilized in its simplest form by surgeons, who grasp (e.g., apply pressure to) unsealed blood vessels with metal forceps and apply radiofrequency current to the forceps via an electrosurgical pen to generate heat and thus effect a seal in the grasped area.

In order to achieve a hyperthermic weld in tissues, several conditions should be met: i) the presence of collagen, and to a lesser degree elastin, at the desired location of the weld and in quantities sufficient to create a weld; ii) an application of pressure, of a degree sufficient to bring adjacent structures into close apposition for intermolecular entanglement and chemical bonding; iii) elevated temperature, of a degree sufficient to denature collagen and/or elastin molecules (e.g., approximately 60° C. and 140° C. respectively); and iv) a sufficient duration of mobility of denatured collagen and elastin.

An excursion at a sufficiently elevated temperature should allow adequate time under favorable conditions for molecular mobility, for collagen and elastin molecules within the tissue to denature (e.g., unravel) and to reconfigure to form the weld. For example, a duration for which water within the tissue is at sufficiently high temperature, yet remains largely in liquid phase to facilitate molecular mobility. An excessive rate of energy delivery can result in desiccation of the target tissue (e.g., loss of mobility of denatured collagen and elastin) before adequate weld strength develops. An insufficient rate of energy delivery will result in inadequate temperatures for collagen and elastin denaturation, which can also result in inadequate weld strength.

Numerous conventional commercial systems, such as VasoView HemoPro® available from Maquet® Cardiovascular LLC of San Jose, Calif., LigaSure™ available from Covidien LLC of Mansfield, Mass., Harmonic® available from Ethicon® LLC of Somerville, N.J., and Olympus PK® available from Olympus Medical® of Japan, are based on the principle of applying heat and pressure to achieve a tissue weld. Heat may be generated within or delivered to the tissue by various modalities, such as radiofrequency energy, ultrasonic energy, or conductive heat transfer. Many conventional commercial instruments deliver bipolar radiofrequency (RF) energy to the target tissues in order to produce the requisite heating. These systems generally deliver RF energy within a narrow frequency band (e.g., 495 kHz) at a constant power output, and employ energy delivery algorithms that sense tissue impedance (via the energy delivery electrodes on the instrument jaws) and automatically shut off power when predetermined impedance-based end conditions are met. Typically, these systems sense (e.g., measure) impedance within the same narrow RF band at which energy is delivered.

SUMMARY

Preferred and non-limiting aspects or embodiments of the present disclosure will now be described in the following numbered clauses:

Clause 1. A biological tissue monitoring system comprising: control circuitry programmed or configured to monitor an impedance of biological tissue, wherein the control circuitry is programmed or configured to: receive or determine an impedance measurement of the biological tissue in response to power delivered to the biological tissue at a plurality of frequencies and a plurality of time points; and adjust or cause to be adjusted the power delivered to the biological tissue at a subsequent time point based on the impedance measurement at the plurality of frequencies and the plurality of time points.

Clause 2. The system of clause 1, wherein the impedance measurement comprises real impedance.

Clause 3. The system of clause 1 or 2, wherein the impedance measurement comprises imaginary impedance.

Clause 4. The system of any of clauses 1-3, wherein the impedance measurement comprises real impedance and imaginary impedance.

Clause 5. The system of any of clauses 1-4, wherein the control circuitry is programmed or configured to determine the impedance measurement based on an average of the real impedance and the imaginary impedance.

Clause 6. The system of any of clauses 1-5, wherein the control circuitry is programmed or configured to determine the impedance measurement based on a weighting of the real impedance that is different than a weighting of the imaginary impedance.

Clause 7. The system of any of clauses 1-6, wherein the control circuitry is programmed or configured to determine the weighting of the real impedance and the weighting of the imaginary impedance dynamically based on an instantaneous impedance span of the impedance measurement at the plurality of frequencies.

Clause 8. The system of any of clauses 1-7, wherein the control circuitry is programmed or configured to determine the weighting of the real impedance and the weighting of the imaginary impedance dynamically based on a rate of change of the impedance measurement at the plurality of frequencies over the plurality of time points.

Clause 9. The system of any of clauses 1-8, wherein the control circuitry is programmed or configured to continuously receive or determine the impedance measurement of the biological tissue.

Clause 10. The system of any of clauses 1-9, wherein the control circuitry is programmed or configured to periodically receive or determine the impedance measurement of the biological tissue.

Clause 11. The system of any of clauses 1-10, wherein the control circuitry is programmed or configured to: determine a rate of change of the impedance measurement of the biological tissue at the plurality of frequencies over the plurality of time points; and adjust or cause to be adjusted the power delivered to the biological tissue at the subsequent time point based on the rate of change of the impedance measurement of the biological tissue at the plurality of frequencies over the plurality of time points.

Clause 12. The system of any of clauses 1-11, wherein the control circuitry is programmed or configured to: receive or determine an average power delivered to the biological tissue at the plurality of frequencies over the plurality of time points; and adjust or cause to be adjusted the power delivered to the biological tissue at the subsequent time point based on the average power.

Clause 13. The system of any of clauses 1-12, wherein the plurality of time points comprise a first time point and a second time point, and wherein the control circuitry is programmed or configured to: determine a difference in the impedance measurement at the plurality of frequencies between the first time point and the second time point; and adjust or cause to be adjusted the power delivered to the biological tissue at the subsequent time point based on the difference in the impedance measurement at the plurality of frequencies between the first time point and the second time point.

Clause 14. The system of any of clauses 1-13, wherein the control circuitry is programmed or configured to adjust or cause to be adjusted the power delivered to the biological tissue at the subsequent time point based on the following equation:

$$P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$$

wherein $P_{tn}$=power delivered to the biological tissue at time tn, $k_A$=scaling constant A where $0 \leq k_A \leq 1$, $\Delta Z_{tn}$=maximum $Z_{real}$–minimum $Z_{real}$, as measured at time tn, and time point t1 occurs before time point t2, which occurs before time point t3.

Clause 15. The system of any of clauses 1-14, wherein the control circuitry is programmed or configured to adjust or cause to be adjusted the power delivered to the biological tissue at the subsequent time point based on the following equation:

$$P_{t3}([P_{t1}+P_{t2}]/2)-k_A*([P_{t1}+P_{t2}]/2)*0.5*([\Delta Z_{real@t2}-\Delta Z_{real@t1}]/[\Delta Z_{real@t2}+\Delta Z_{real@t1}]+([\Delta Z_{imag@t2}-\Delta_{imag@t1}]/[\Delta Z_{imag@t2}+\Delta Z_{imag@t1}])$$

wherein $P_{tn}$=power delivered to the biological tissue at time tn, $k_A$=scaling constant A where $0 \leq k_A \leq 1$, time point t1 occurs before time point t2, which occurs before time point t3, $\Delta Z_{real@tn}$=maximum Zreal–minimum Zreal, as measured at time tn, and $\Delta Z_{imag@tn}$=maximum Zimag–minimum Zimag, as measured at time tn.

Clause 16. The system of any of clauses 1=15, wherein the control circuitry is programmed or configured to adjust or cause to be adjusted the power delivered to the biological tissue at the subsequent time point based on the following equation:

$$P_{t3}([P_{t1}+P_{t2}]/2)-k_r*([P_{t1}+P_{t2}]/2)*([\Delta Z_{real@t2}-\Delta Z_{real@t1}]/[\Delta Z_{real@t2}+\Delta Z_{real@t1}]-k_i*([P_{t1}+P_{t2}]/2)*[\Delta Z_{imag@t2}-\Delta_{imag@t1}]/[\Delta Z_{imag@t2}+\Delta Z_{imag@t1}]$$

wherein $k_r$ and $k_i$ are scaling constants for real and imaginary portions respectively, $P_{tn}$=power delivered to the biological tissue at time tn, time point t1 occurs before time point t2, which occurs before time point t3, $\Delta Z_{real@tn}$=maximum Zreal–minimum Zreal, as measured at time tn, and $\Delta Z_{imag@tn}$=maximum Zimag–minimum Zimag, as measured at time tn.

Clause 17. The system of any of clauses 1-16, wherein the control circuitry is programmed or configured to: determine a weld end point, an ablation endpoint, or an error condition based on at least one of a real impedance component of the impedance measurement and an imaginary impedance component of the impedance measurement; and terminate or cause to be terminated the power delivered to the biological tissue based on the determination of the weld end point, the ablation endpoint, or the error condition.

Clause 18. The system of any of clauses 1-17, wherein the control circuitry is programmed or configured to: determine based on the impedance measurement at the plurality of frequencies and the plurality of time points at least one of a tissue condition and weld stage of the biological tissue.

Clause 19. The system of any of clauses 1-18, wherein the at least one of the tissue condition and the weld stage of the biological tissue are determined based on a magnitude of change in the impedance measurement at the plurality of frequencies over the plurality of time points.

Clause 20. The system of any of clauses 1-19, wherein the control circuitry is programmed or configured to: increase an amount of time that the biological tissue spends in a particular weld stage by decreasing or causing to be decreased the power delivered to the biological tissue at the subsequent time point.

Clause 21. The system of any of clauses 1-20, wherein the control circuitry is programmed or configured to: decrease an amount of time that the biological tissue spends in a particular weld stage by increasing or causing to be increased the power delivered to the biological tissue at the subsequent time point.

Clause 22. The system of any of clauses 1-21, wherein the control circuitry is programmed or configured to: determine based on the impedance measurement at the plurality of frequencies and the plurality of time points a current weld stage of the biological tissue; and adjust or cause to be adjusted the power delivered to the biological tissue at the subsequent time point based on the current weld stage of the biological tissue.

Clause 23. The system of any of clauses 1-22, wherein the current weld stage comprises one of: a first stage in which the biological tissue is in an initial tissue state and cell membranes of the biological tissue are substantially intact; a second stage in which the biological tissue is being heated and the cell membranes begin to rupture; a third stage in which the biological tissue is continued to be heated and the rupture of the cell membranes is substantially complete; a fourth stage in which the biological tissue is continued to be heated and a limited amount of tissue desiccation can occur, but moisture content of the biological tissue remains substantially near a peak moisture content, in liquid phase, with substantially minimal loss through vaporization; a fifth stage in which substantial tissue desiccation begins; a sixth stage in which tissue desiccation is substantially complete; and a seventh stage in which tissue desiccation is complete.

Clause 24. The system of any of clauses 1-23, wherein the control circuitry is programmed or configured to: during a first weld stage, adjust or cause to be adjusted the power delivered to the biological tissue at the subsequent time point based on a first power adjustment algorithm; and during a second weld stage, adjust or cause to be adjusted the power delivered to the biological tissue at the subsequent time point based on a second power adjustment algorithm different than the first power adjustment algorithm.

Clause 25. The system of any of clauses 1-24, wherein the first power adjustment algorithm is more sensitive to changes in the impedance measurement at the plurality of frequencies and the plurality of time points than the second power adjustment algorithm.

Clause 26. The system of any of clauses 1-15, wherein the first power adjustment algorithm is based on the impedance measurement at the plurality of frequencies and the plurality of time points, and wherein the second power adjustment algorithm is based on a single-frequency impedance measurement.

Clause 27. The system of any of clauses 1-26, wherein the control circuitry is programmed or configured to modify a timing of an adjustment of the power delivered to the biological tissue based on the impedance measurement.

Clause 28. The system of any of clauses 1-27, wherein the impedance measurement at the plurality of frequencies and the plurality of time points satisfies at least one threshold.

Clause 29. The system of any of clauses 1-28, wherein the at least one threshold comprises at least one of a minimum power level and maximum power level.

Clause 30. The system of any of clauses 1-29, wherein at least one threshold comprises a minimum change in the impedance measurement over the plurality of frequencies at a time point.

Clause 31. The system of any of clauses 1-30, wherein the control circuitry is programmed or configured to adjust or cause to be adjusted the power delivered to the biological tissue at the subsequent time point by comparing the impedance measurement to a look-up table.

Clause 32. The system of any of clauses 1-31, wherein the impedance measurement is at set of predetermined frequencies.

Clause 33. The system of any of clauses 1-32, wherein the impedance measurement is at a predetermined number of discrete waveforms.

Clause 34. The system of any of clauses 1-33, wherein the control circuitry is programmed or configured to bin the impedance measurement into one frequency bin of a plurality of frequency bins based on the frequency of the impedance measurement.

Clause 35. The system of any of clauses 1-34, wherein the control circuitry is programmed or configured to determine at least one of a type of the biological tissue, a status of the biological tissue, and an amount of the biological tissue based on the impedance measurement at the plurality of frequencies and the plurality of time points.

Clause 36. The system of any of clauses 1-35, wherein the type of tissue identifies at least one of muscle or fat tissue, ischemic or infarcted tissue, and normal or cancerous tissue.

Clause 37. The system of any of clauses 1-36, wherein the determination is further based on at least one of a duration of a weld stage and an amount of impedance change between two weld stages.

Clause 38. The system of any of clauses 1-37, wherein the control circuitry is programmed or configured to adjust or cause to be adjusted the power delivered to the biological tissue at the subsequent time point based on the following equation:

IF [$\Delta Z_{real@tn}$=minimum value of Zreal]

OR ([minimum Zreal has been reached] AND [$\Delta Z_{real@tn} \leq 120\%$ of minimum Zreal])

THEN $P_{t3}=0.9*([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ ELSE $P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ wherein $P_{tn}$=power delivered to the biological tissue at time tn, $k_A$=scaling constant A where $0 \leq k_A \leq 1$, $\Delta Z_{real@tn}$=maximum $Z_{real}$–minimum $Z_{real}$, as measured at time tn, and time point t1 occurs before time point t2, which occurs before time point t3.

Clause 39. The system of any of clauses 1-38, wherein the control circuitry is programmed or configured to adjust or cause to be adjusted the power delivered to the biological tissue at the subsequent time point based on the following equation:

IF ([minimum Zreal has been reached] AND [$\Delta Z_{real@tn} \geq 120\%$ of minimum Zreal])

THEN $P_{t3}=0.75*([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ ELSE $P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ wherein $P_{tn}$=power delivered to the biological tissue at time tn, $k_A$=scaling constant A where $0 \leq k_A \leq 1$, $\Delta Z_{real@tn}$=maximum $Z_{real}$–minimum $Z_{real}$, as measured at time tn, and time point t1 occurs before time point t2, which occurs before time point t3.

Clause 40. The system of any of clauses 1-39, wherein the control circuitry is programmed or configured to adjust or cause to be adjusted the power delivered to the biological tissue at the subsequent time point based on the following equation:

IF [minimum Zreal has not been reached]

THEN $P_{t3}=1.25*([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ ELSE $P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ wherein $P_{tn}$=power delivered to the biological tissue at time tn, $k_A$=scaling constant A where $0 \leq k_A \leq 1$, $\Delta Z_{tn}$=maximum $Z_{real}$–minimum $Z_{real}$, as measured at time tn, and time point t1 occurs before time point t2, which occurs before time point t3.

Clause 41. The system of any of clauses 1-40, wherein the control circuitry is programmed or configured to: adjust or cause to be adjusted the power delivered to the biological tissue at the subsequent time point based on a power adjustment algorithm used to control the power delivery to the tissue; and dynamically adjust parameters of the power adjustment algorithm used to control the power delivered to the tissue based on the impedance measurement.

Clause 42. The system of any of clauses 1-41, wherein the control circuitry is programmed or configured to: determine at least one of a type and a condition of the biological tissue based on the impedance measurement; and dynamically adjust the parameters of the power adjustment algorithm used to control the power delivered to the tissue based on the at least one of the determined type and the determined condition of the biological tissue.

Clause 43. The system of any of clauses 1-42, wherein the control circuitry is programmed or configured to determine the at least one of the type and the condition of the biological tissue based on an amount of time a real component of the impedance measurement takes to reach a threshold value.

Clause 44. The system of any of clauses 1-43, wherein the control circuitry is programmed or configured to determine the at least one of the type and the condition of the biological tissue based on an amount of time a real component of the impedance remains below a threshold value after reaching a minimum value.

Clause 45. A biological tissue monitoring system comprising: control circuitry programmed or configured to monitor an impedance of biological tissue, wherein the control circuitry is programmed or configured to: receive or determine an impedance measurement of the biological tissue in response to power delivered to the biological tissue at a plurality of frequencies and a plurality of time points; determine at least one of a type of the biological tissue, a status of the biological tissue, and an amount of the biological tissue based on the impedance measurement at the plurality of frequencies and the plurality of time points.

Clause 46. The system of clause 45, wherein the control circuitry is programmed or configured to determine the type of biological tissue based on a comparison of an initial impedance measurement of the biological tissue to known characteristic electrical properties of biological tissue, and a temperature response of the impedance measurement to the power delivered to the biological tissue.

Clause 47. The system of clause 45 or 46, wherein the control circuitry is programmed or configured to determine the status of the tissue based on an initial impedance measurement of the biological tissue and a duration and an amount of change in the impedance measurement from a first weld stage to a second weld stage.

Clause 48. The system of any of clauses 45-47, wherein the control circuitry is programmed or configured to determine the amount of tissue based on an initial impedance measurement of the biological tissue, an amount of change in the impedance measurement from a first weld stage to a second weld stage, an amount of time required to reach the second weld stage, and a duration of a third weld stage.

Clause 49. A biological tissue monitoring system comprising: control circuitry programmed or configured to monitor an impedance of biological tissue, wherein the control circuitry is programmed or configured to: receive or determine an impedance measurement of the biological tissue in response to power delivered to the biological tissue at at least two frequencies and at least one time point; and adjust or cause to be adjusted the power delivered to the biological tissue at a subsequent time point based on the impedance measurement at the at least two frequencies and the at least one time point.

Clause 50. A biological tissue monitoring system comprising: control circuitry configured to monitor an impedance of biological tissue, wherein the control circuitry is programmed or configured to: receive or determine an impedance measurement of the biological tissue in response to power delivered to the biological tissue at a plurality of frequencies and a plurality of time points; determine when the impedance measurement of the biological tissue is at a substantially minimum value; and control or cause to be controlled the power delivered to the biological tissue to prolong the impedance measurement of the biological tissue at the substantially minimum value.

Clause 51. The system of clause 50, wherein the control circuitry is programmed or configured to: control or cause to be controlled the power delivered to the biological tissue based on a power adjustment algorithm; and modify the power adjustment algorithm to prolong the impedance measurement of the biological tissue at the substantially minimum value.

Clause 52. The system of clause 50 or 51, wherein the control circuitry is programmed or configured to: modify one or more scaling constants of the power adjustment algorithm.

Clause 53. A biological tissue monitoring system comprising: control circuitry configured to monitor an impedance of biological tissue, wherein the control circuitry is programmed or configured to: receive or determine an impedance measurement of the biological tissue in response to power delivered to the biological tissue at a plurality of frequencies and a plurality of time points; determine based on the impedance measurement that the biological tissue is in a particular weld stage; and modify a power adjustment algorithm used to determine the power delivery to the biological tissue based on the impedance measurement of the tissue.

Clause 54. The system of clause 53, wherein the control circuitry is programmed or configured to: modify the power adjustment algorithm to achieve a desired decrease in the power delivered to the biological tissue.

Clause 55. A biological tissue monitoring system comprising: control circuitry programmed or configured to monitor an impedance of biological tissue, wherein the control circuitry is programmed or configured to: receive or determine an impedance measurement of the biological tissue at an instantaneous point in time in response to power delivered to the biological tissue at a plurality of frequencies; and adjust or cause to be adjusted the power delivered to the biological tissue at a subsequent time point based on the impedance measurement at the plurality of frequencies at the instantaneous point in time.

Clause 56. The system of clause 55, wherein the control circuitry is programmed or configured to: compare the impedance measurement at the instantaneous point in time to characteristic electrical properties of a plurality of tissue types to determine a tissue type of the plurality of tissue types that corresponds to biological tissue.

Clause 57. The system of clause 55 or 56, wherein the control circuitry is programmed or configured to: select a power adjustment algorithm to control the power delivered to the biological tissue at the subsequent time point from a plurality of predetermined algorithms based on the impedance measurement at the plurality of frequencies at the instantaneous point in time.

Clause 58. The system of any of clauses 55-57, further comprising: a generator configured to deliver the power to biological tissue at the plurality of frequencies; and at least one sensor configured to measure the impedance of the biological tissue at the instantaneous point in time in response to the power delivered to the biological tissue at the plurality of frequencies, wherein the control circuitry is programmed or configured to control the generator to adjust the power delivered to the biological tissue at the subsequent point in time based on the impedance measurement at the plurality of frequencies at the instantaneous point in time.

Clause 59. A target mass monitoring system comprising: a generator configured to generate power at a plurality of frequencies and a plurality of time points; an instrument configured to deliver the power to a target mass at the plurality of frequencies and the plurality of time points; at least one sensor configured to measure the impedance of the target mass in response to the power delivered to the target mass at the plurality of frequencies and the plurality of time points; and a controller configured to adjust or cause to be adjusted the power delivered to the target mass at a subsequent time point based on the impedance measurement at the plurality of frequencies and the plurality of time points.

Clause 60. The system of clause 59, wherein the impedance measurement comprises at least one of real impedance and imaginary impedance.

Clause 61. The system of clause 59 or 60, wherein the controller is configured to determine the impedance measurement based on an average of the real impedance and the imaginary impedance.

Clause 62. The system of any of clauses 59-61, wherein the controller is configured to determine the impedance measurement based on a weighting of the real impedance that is different than a weighting of the imaginary impedance.

Clause 63. The system of any of clauses 59-62, wherein the controller is configured to: determine a rate of change of the impedance measurement of the target mass at the plurality of frequencies over the plurality of time points; and adjust or cause to be adjusted the power delivered to the target mass at the subsequent time point based on the rate of change of the impedance measurement of the target mass at the plurality of frequencies over the plurality of time points.

Clause 64. The system of any of clauses 59-63, wherein the controller is configured to: adjust or cause to be adjusted the power delivered to the target mass at the subsequent time point based on a power adjustment algorithm used to control the power delivery to the target mass; and dynamically adjust parameters of the power adjustment algorithm used to control the power delivered to the tissue based on the impedance measurement.

Clause 65. The system of any of clauses 59-64, wherein the controller is configured to: determine at least one of a type and a condition of the target mass based on the impedance measurement; and dynamically adjust the parameters of the power adjustment algorithm used to control the power delivered to the tissue based on the at least one of the determined type and the determined condition of the target mass.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 3 is a chart of example weld stages of soft tissue;

DETAILED DESCRIPTION

Figure 1A:
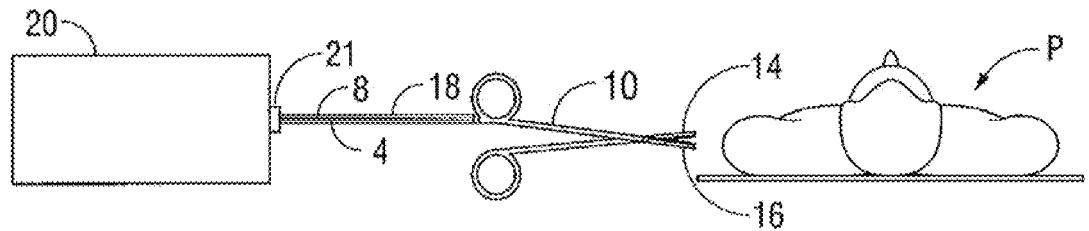
FIG. 1A is a schematic block diagram of a bipolar electrosurgical system.

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the embodiments disclosed as it is oriented in the drawing figures. However, it is to be understood that the embodiments disclosed can assume various alternative orientations and, accordingly, such terms are not to be considered as limiting. Also, it is to be understood that the embodiments disclosed can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Aspects of the present disclosure are directed to systems and methods for power adjustment that utilize closed loop energy delivery to a target mass and/or for biological tissue welding, using broadband impedance spectroscopy (BIS) data measured by an electrosurgical generator to determine adjustments to power delivered at instrument electrodes to the target mass and/or the tissue and/or a condition and weld stage of the target mass and/or the tissue. An impedance measurement may be a singular measurement or multiple measurements. The power adjustments disclosed herein can improve weld strength of the biological tissue by providing optimal conditions for weld formation and for weld completion, as well as optimize other aspects such as weld duration and extent of lateral thermal damage.

A generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency (RF) power specifically suited for various electrosurgical modes (e.g., cutting, blending, division, etc.) and procedures (e.g., monopolar, bipolar, vessel sealing). In an example, the electronic circuitry is configured to generate the RF power simultaneously at multiple low and high frequencies and/or simultaneously across a range of different frequencies or different frequency bands, and to simultaneously measure the frequency-dependent response of the biological tissue to the RF power to infer the state of individual tissue constituents. For example, the electronic circuitry of the generator can generate the RF power at a set of predetermined frequencies, e.g., 2 MHz, 1.5 MHz, 1 MHz, 750 kHz, 500 kHz, 250 kHz, or across a larger range, such as at 0 Hz through 10 MHz at 1.25 kHz intervals).

Figure 1B:
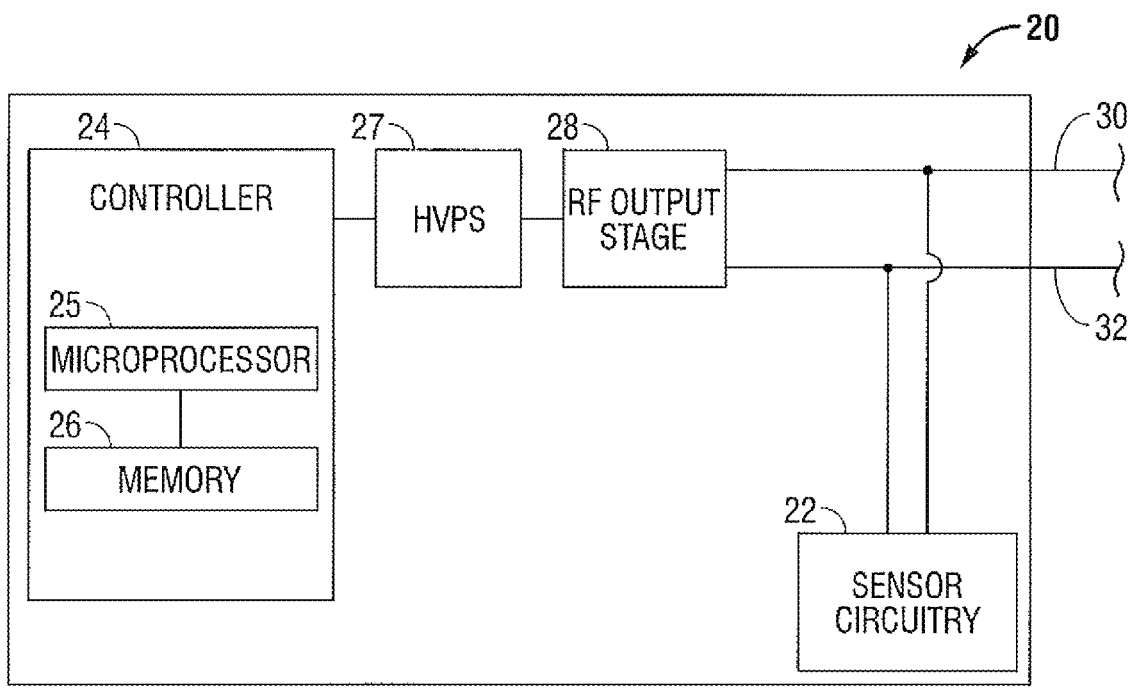
FIG. 1B is a schematic block diagram of a generator.

FIG. 1A is a schematic illustration of a bipolar electrosurgical system. The system includes a bipolar electrosurgical instrument 10, 110 having one or more electrodes for treating tissue of a patient P. In other implementations, the system may include a bipolar RF epicardial clamp device 710, a RF epicardial ablation device 810a, a RF endocardial ablation catheter 810b, or soft tissue ablation device 910 as described in more detail herein with respect to FIGS. 7, 8A, 8B, and 9, respectively. The electrosurgical instrument 10, 110 includes opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 1B). The electrosurgical instrument 10, may be configured as a forceps 10 or alternatively may be configured as a laparoscopic tool 110 comprising a handle 17, and end effector 13 (such as a set of jaws with electrodes secured thereto), and a shaft 15 extending between the handle 17 and the end effector 13. The electrosurgical instrument 10, 110 is coupled to the generator 20 at a connector 21 having connections to the active and return terminals 30 and 32 (e.g., pins) via a plug disposed at the end of the cable 18, wherein the plug includes contacts from the supply and return lines 4, 8. An set of examples of electrosurgical instrument 110 and its respective applications for use with the embodiments of the present disclosure may include those disclosed and described in the following applications, the entireties which are incorporated herein by reference: (i) U.S. Provisional Application Ser. No. 62/109,920, filed Jan. 30, 2015 at the United States Patent and Trademark Office, (ii) U.S. Provisional Application Ser. No. 62/109,910, filed Jan. 30, 2015 at the United States Patent and Trademark Office, (iii) U.S. Provisional Application Ser. No. 62/104,389, filed Jan. 16, 2015 at the United States Patent and Trademark Office, (iv) U.S. Provisional Application Ser. No. 62/099,667, filed Jan. 5, 2015 at the United States Patent and Trademark Office, (v) U.S. Provisional Application Ser. No. 62/092,992, filed Dec. 17, 2014 at the United States Patent and Trademark Office, (vi) U.S. Provisional Application Ser. No. 62/092,985, filed Dec. 17, 2014 at the United States Patent and Trademark Office, (vii) U.S. Provisional Application Ser. No. 62/092,981, filed Dec. 17, 2014 at the United States Patent and Trademark Office, (viii) U.S. Provisional Application Ser. No. 62/092,974, filed Dec. 17, 2014 at the United States Patent and Trademark Office, (ix) U.S. Provisional Application Ser. No. 62/092,966, filed Dec. 17, 2014 at the United States Patent and Trademark Office, (x) U.S. Provisional Application Ser. No. 62/092,951, filed Dec. 17, 2014 at the United States Patent and Trademark Office, (xi) International PCT Application serial number PCT/US15/66468, filed Dec. 17, 2015 at the United States Patent and Trademark Office, (xii) International PCT Application serial number PCT/US15/66405, filed Dec. 17, 2015 at the United States Patent and Trademark Office, (xiii) International PCT Application serial number PCT/US15/66381, filed Dec. 17, 2015 at the United States Patent and Trademark Office, (xiv) International PCT Application serial number PCT/US15/66376, filed Dec. 17, 2015 at the United States Patent and Trademark Office, and (xv) International PCT Application serial number PCT/US15/66354, filed Dec. 17, 2015 at the United States Patent and Trademark Office.

The generator 20 includes suitable input controls (e.g., buttons, activators, switches, touch screen, etc.) for controlling the generator 20. The generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.). The instrument 10, 110 may also include a plurality of input controls that may be redundant with certain input controls of the generator 20. Placing the input controls at the instrument 10, 110 allows for easier and faster modification of RF energy parameters during the surgical procedure without requiring interaction with the generator 20.

FIG. 1B shows a schematic block diagram of the generator 20 having a controller 24, a high voltage DC power supply 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

For example, the RF output stage 28 can generate sinusoidal waveforms of high RF energy. The RF output stage 28 is configured to generate a plurality of waveforms having various duty cycles, peak voltages, crest factors, frequencies, and other suitable parameters. In one implementation, the RF output stage 28 is configured to generate a waveform for performing BIS measurements (e.g., by the sensor circuitry 22). Certain types of waveforms are suitable for specific electrosurgical modes. For example, the RF output stage 28 can generate a 10, 1100% duty cycle sinusoidal waveform in cut mode, which is better suited for ablating, fusing and dissecting tissue and a 1-25% duty cycle waveform in coagulation mode, which is better for cauterizing tissue to stop bleeding. As described herein, waveforms providing BIS measurements are advantageous for controlling power delivery to tissue during a weld. For example, the RF output stage 28 can generate power to be delivered to the biological tissue at a plurality of frequencies (e.g., at a plurality of frequency bands, such as such as at 0 Hz through 10 MHz at 1.25 kHz intervals) and a plurality of time points.

The generator 20 may include a plurality of connectors to accommodate various types of electrosurgical instruments (e.g., electrosurgical forceps 10, electrosurgical laparoscopic instrument 110, bipolar RF epicardial clamp device 710, RF epicardial ablation device 810a, RF endocardial ablation catheter 810b, or soft tissue ablation device 910, etc.). Further, the generator 20 is configured to operate in a variety of modes such as ablation, monopolar and bipolar cutting coagulation, etc. The generator 20 may include a switching mechanism (e.g., relays) to switch the supply of RF energy between the connectors, such that, for instance, when the instrument 10, 110 is connected to the generator 20, only the bipolar plug receives RF energy.

The controller 24 includes a microprocessor 25 operably connected to a memory 26, which may be volatile type memory (e.g., RAM) and/or non-volatile type memory (e.g., flash media, disk media, etc.). For example, the controller 24 can include a processor commercially available from companies such as Texas Instruments, Intel, AMD, IBM, Freescale and ARM Holdings. The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuitry 22, which may include a plurality of sensors measuring a variety of tissue and energy properties (e.g., tissue impedance, tissue temperature, output current and/or voltage, voltage and current passing through the tissue, etc.), provides feedback to the controller 24. Such sensors are within the purview of those skilled in the art. The controller 24 signals the HVPS 27 and/or RF output stage 28, which adjust DC and/or RF power supply, respectively. The controller 24 also receives input signals from the input controls of the generator 20 or the instrument 10, 110. The controller 24 utilizes the input signals to adjust power outputted by the generator 20 and/or performs other control functions thereon.

In some implementations, the controller 24 can comprise a smartphone, a personal digital assistant (PDA), a laptop, a tablet personal computer (PC), a desktop PC, a server computer, or any other type of computing device capable of controlling the HVPS 27 and/or the RF output stage 28 and processing of the BIS data as described herein. Although shown as part of the generator 20 in FIG. 2, the controller 24 and/or the sensor circuitry can be a remote computing device connected to the instrument 10, 110 (or the bipolar RF epicardial clamp device 710, the RF epicardial ablation device 810a, the RF endocardial ablation catheter 810b, or the soft tissue ablation device 910), and/or the generator 20 via wired or wireless communication to control or adjust the delivery of the power to the biological tissue from the instrument 10, 110 (or the bipolar RF epicardial clamp device 710, the RF epicardial ablation device 810a, the RF endocardial ablation catheter 810b, or the soft tissue ablation device 910) or the output of the power from the generator 20. In another example, the instrument 10, 110 (or the bipolar RF epicardial clamp device 710, the RF epicardial ablation device 810a, the RF endocardial ablation catheter 810b, or the soft tissue ablation device 910) can comprise hardware and software for implementing the controller 24 and/or the sensor circuitry 22 such that the power adjustment and processing and/or measuring of the BIS data is performed by the instrument 10, 110 (or the bipolar RF epicardial clamp device 710, the RF epicardial ablation device 810a, the RF endocardial ablation catheter 810b, or the soft tissue ablation device 910). For example, the at least one processor of the controller 24 is configured to determine or receive the BIS data and adjust the output of the power delivered to the biological tissue based on the BIS data, and/or to determine a condition and weld status of the biological tissue.

Figure 2A:
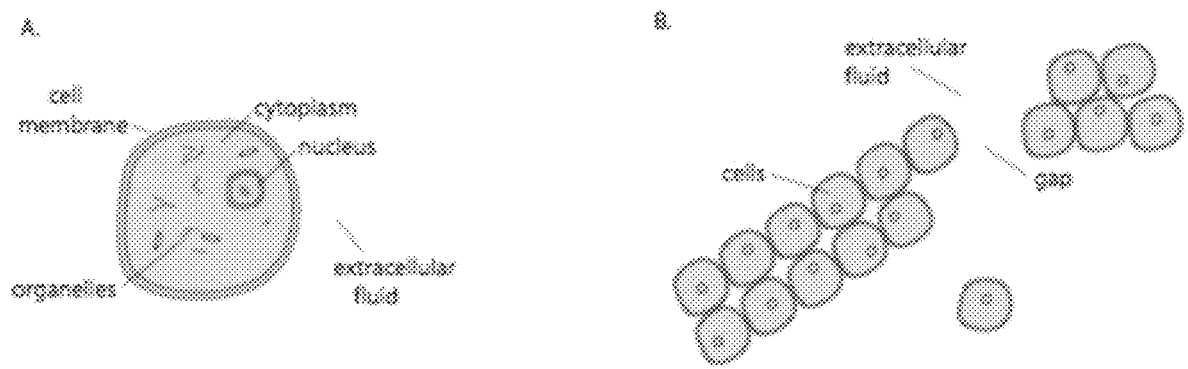
FIG. 2A is a diagram of an example cellular arrangement of soft tissue.

Soft biological tissue (e.g., muscle and fat) can be electrically modeled by using circuit elements to represent tissue constituents at a subcellular level as shown in the FIG. 2A and Table 1 described in further detail below. Referring to FIG. 2A, the left side A.) is a simplified diagram of a single cell, which size can vary between 10 um to about 1 mm, and the right side B) is a diagram of tissue composed of collections of cells. Gaps between the cells allow current to flow through shunt paths formed by interstitial fluids. Table 1 below shows the electrical behavior and electrical representation of various soft tissue constituents.

TABLE 1

| Soft tissue constituent | Electrical behavior | Electrical representation |
| --- | --- | --- |
| Cell membrane (lipid bilayer) | Insulative | Capacitor |
| Cytoplasm (intracellular fluid, in liquid state) | Conductive | Resistor |
| Interstitial fluid (extracellular fluid, in liquid state) | Conductive | Resistor |

Figure 2B:
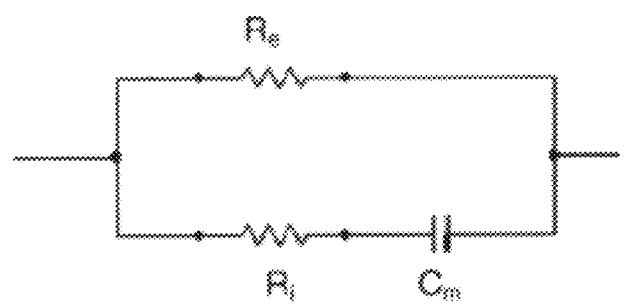
FIG. 2B is a circuit diagram for modeling soft tissue behavior.

The aggregate behavior of the soft tissue constituents can be modeled as a parallel R-RC circuit, as shown in FIG. 2B. $R_i$ and $R_e$ represent resistances of intracellular and extracellular spaces, respectively. $C_m$ represents cell membrane capacitance. When measuring electrical impedance, the response of components of the circuit shown in FIG. 2B vary with frequency. At low frequencies (e.g., 0 Hz), intact cell membranes behave as capacitive members, preventing electrical current flow through the conductive cytoplasm and limiting current flow to the interstitial fluid. At high frequencies (e.g., 2 MHz), those same cell membranes are electrically permeable, allowing current flow through the cytoplasm (in addition to the interstitial fluid). Individual tissue constituents are altered in form, composition, and/or proportion during the course of a hyperthermic weld, for example, cell membranes are ruptured, and water is evaporated, thereby also changing the aggregate-behavior electrical model and associated frequency response.

By using a more advanced sensing system, namely broadband impedance spectroscopy (BIS), it is possible to glean additional information about underlying phenomena occurring in the tissue during a weld. This additional information can be obtained by measuring tissue impedance at low and high frequencies, or across a range of frequencies or frequency bands, and by using the frequency-dependent response of the tissue to infer the state of individual tissue constituents.

FIG. 3 is a chart of example weld stages of soft tissue. FIG. 3 shows measurements based on an example weld using a generic power delivery algorithm (i.e., constant peak power), with weld stages, tissue effects (inferred from BIS data), and underlying BIS-based rationale outlined in the accompanying table. FIGS. 4A-G are scatter graphs of example impedance values of soft tissue in example weld stages. In each of the graphs in FIGS. 4A-G, real impedances and imaginary impedances are displayed on the x-axis and y-axis, respectively. Each datum point on the scatter graph represents a different measurement frequency; light-colored data points denote low-frequency measurements, with datum point color becoming progressively darker as measurement frequency increases. For example, FIGS.

4A-G respectively correspond to weld stages A, B, C, D, E/F, G, and H as shown in FIG. 3.

Figure 4A:
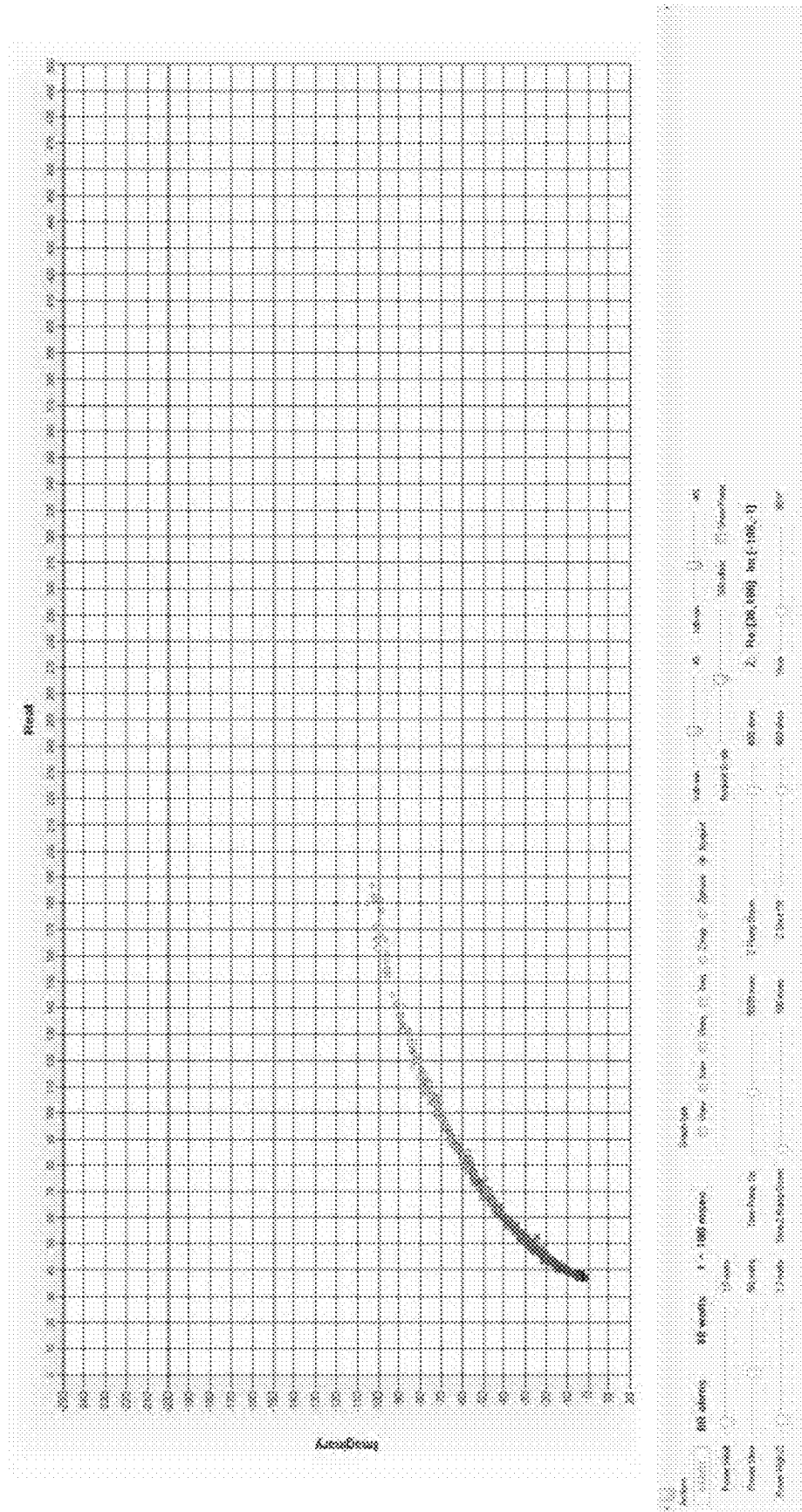
FIGS. 4A-G are scatter graphs of example impedance values of soft tissue in example weld stages.
Figure 4B:
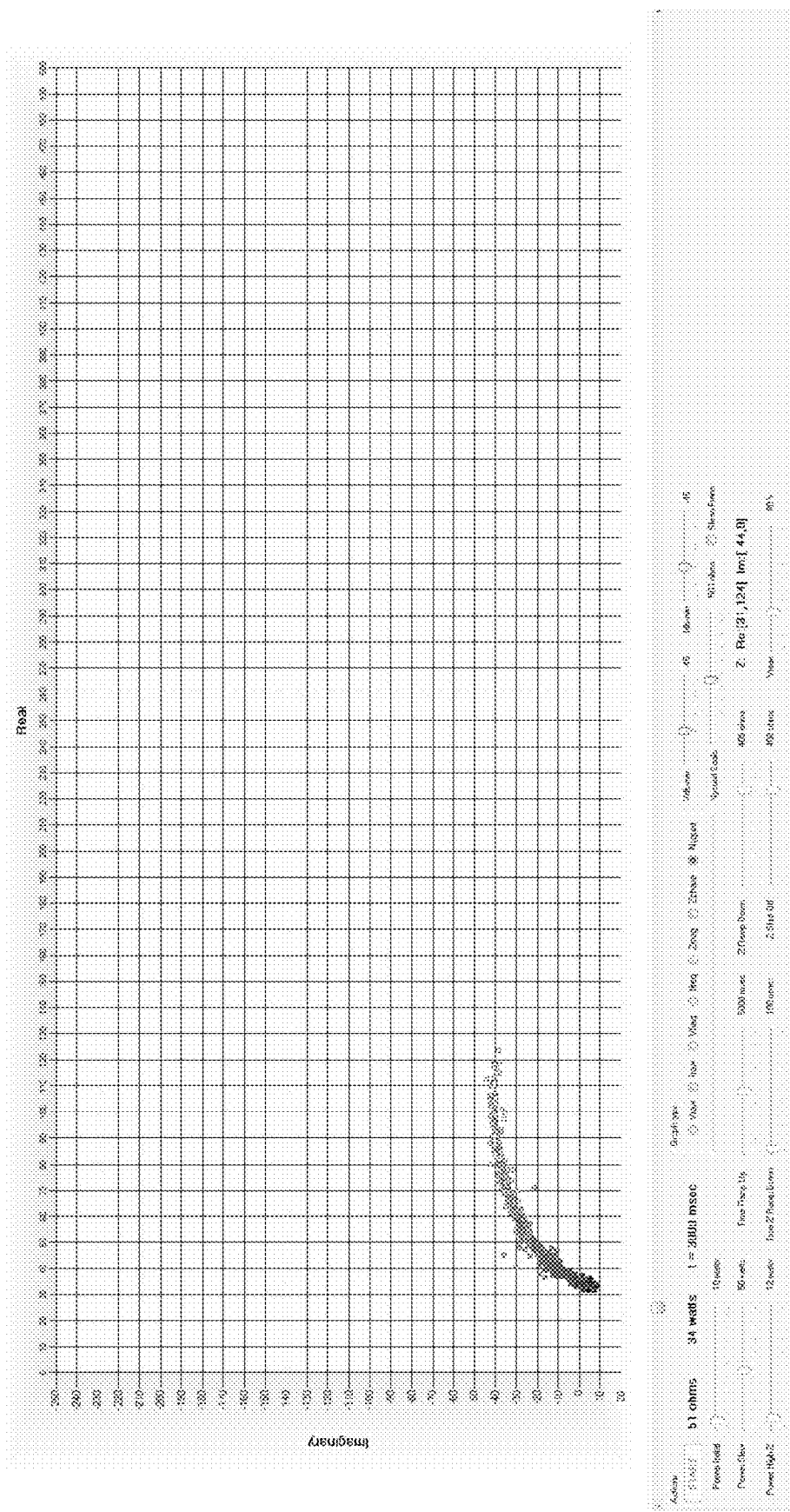
Figure 4C:
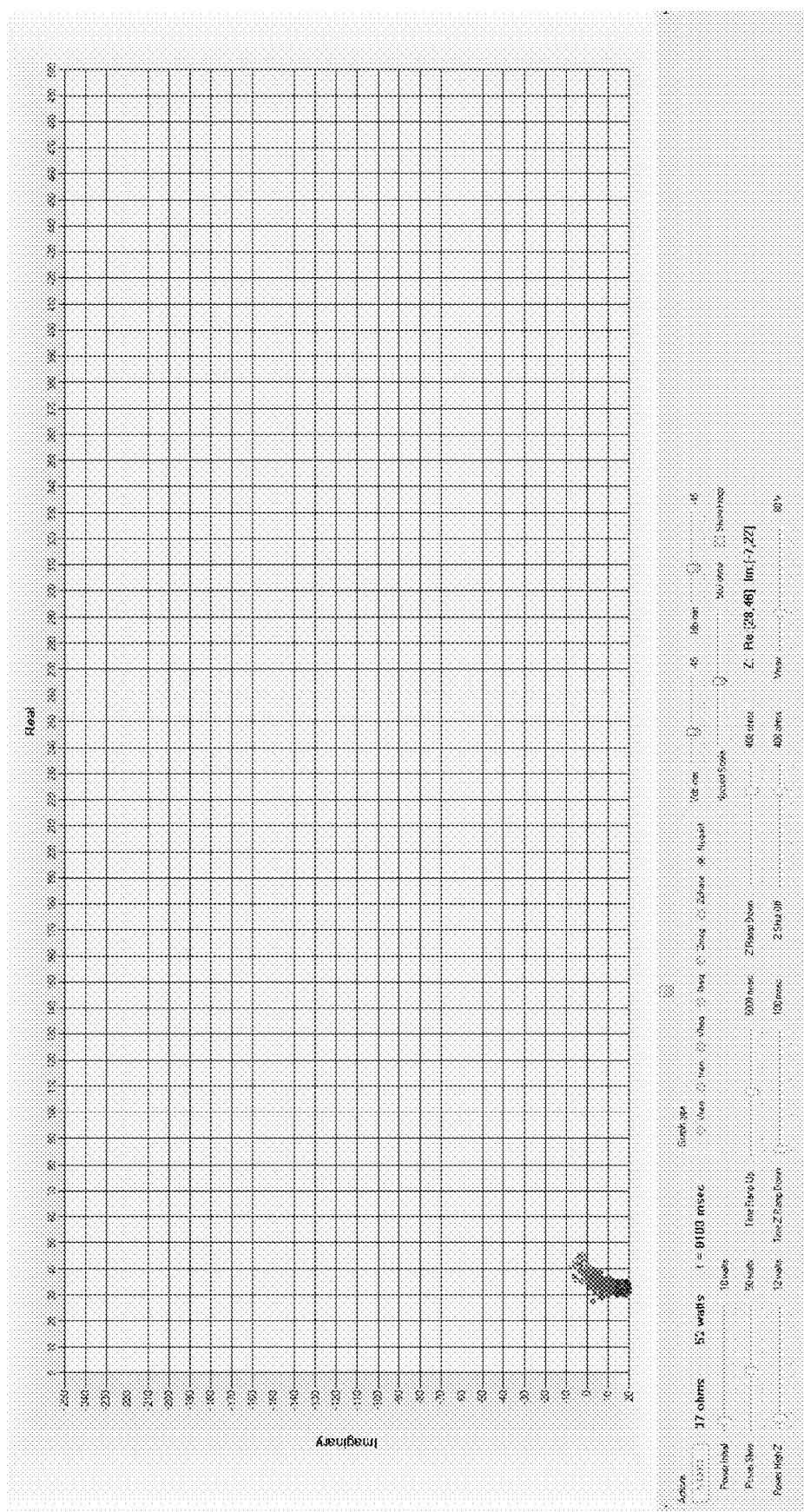
Figure 4D:
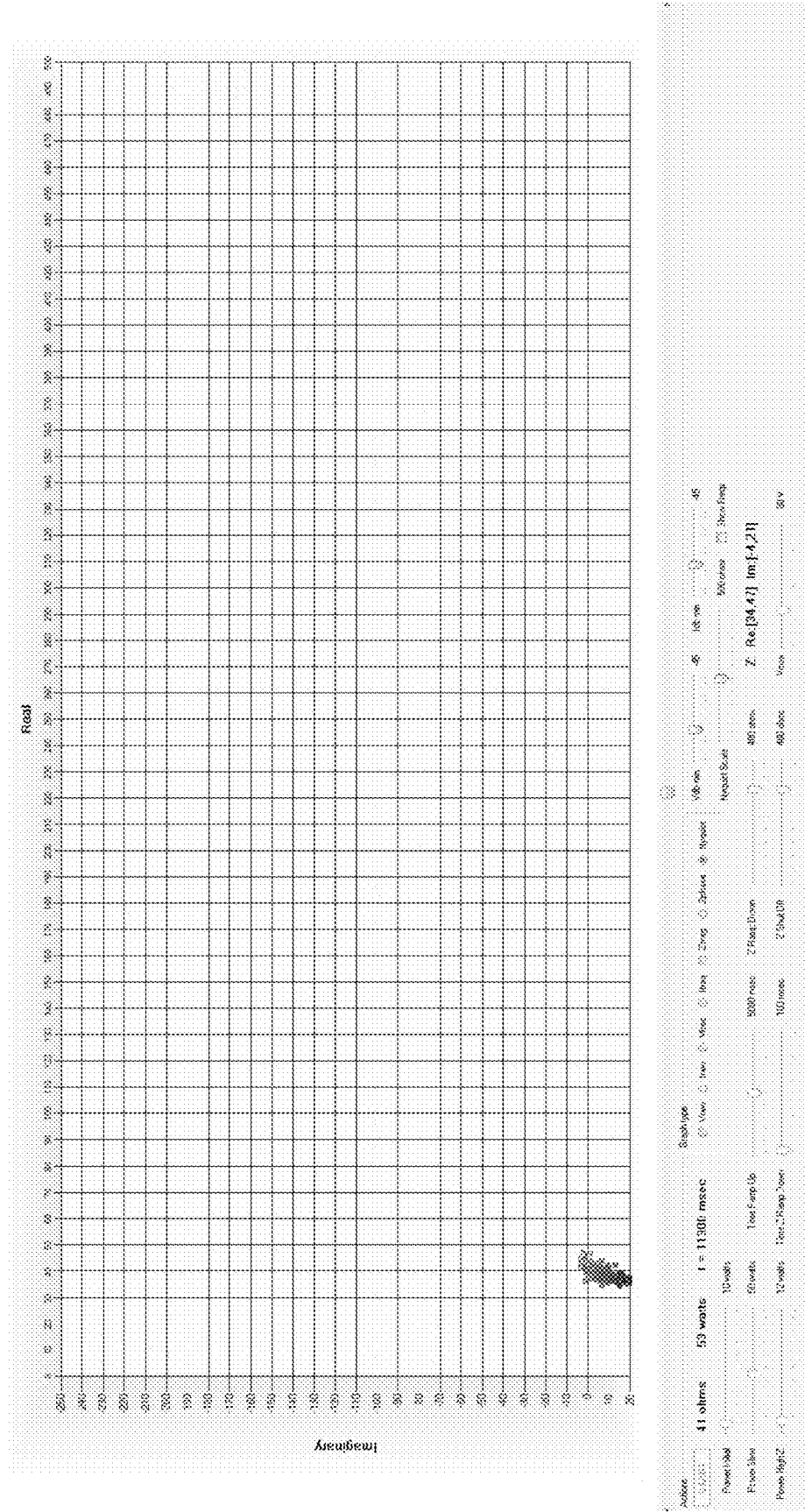

FIG. 4A, which corresponds to Stage A, shows measurements taken on naive/untreated tissue at the start of power delivery. Electrical current only flows through interstitial fluid at lower frequencies, but electrical current flows through both interstitial fluid and cytoplasmic fluid at higher frequencies. $Z_{real}$ values at lower frequencies are thus greater than at higher frequencies due to the capacitive contribution of the intact cell membranes. As shown in FIG. 4B, which corresponds to Stage B, as tissue heating begins and cell membrane rupture commences, overall values of $Z_{real}$ decrease as tissue temperature increases, and $Z_{real}$ values at lower frequencies decrease due to current flow through cytoplasmic fluids released from ruptured cells. As shown in FIG. 4C, which corresponds to Stage C, rupture of cell membranes is substantially complete, and minimum values of $Z_{real}$ are reached as the combination of interstitial and cytoplasmic fluids (the latter no longer impeded by intact cell membranes) increases overall electrical conductivity, with increased tissue temperatures further enhancing the overall electrical conductivity. Moisture content of the tissue is near its peak, as evidenced by the minimum values of $Z_{real}$, with water in the tissue continuing to absorb energy but remaining predominantly in liquid phase. It is at Stage C that weld formation begins, under a combination of elevated temperature (which causes denaturation of collagen and elastin molecules), applied pressure (for apposition of the tissues to be welded), and high liquid content (for mobility of the denatured collagen and elastin molecules). As shown in FIG. 4D, which corresponds to Stage D, tissue heating continues, and although a limited amount of tissue desiccation occurs from loss of water vapor, moisture content remains near its peak and in liquid phase, as evidenced by a minimal increase in $Z_{real}$ values from Stage C. The majority of weld formation occurs during Stage D due to the combination of elevated temperature, applied pressure, and high molecular mobility for a substantial period of time.

Figure 4E:
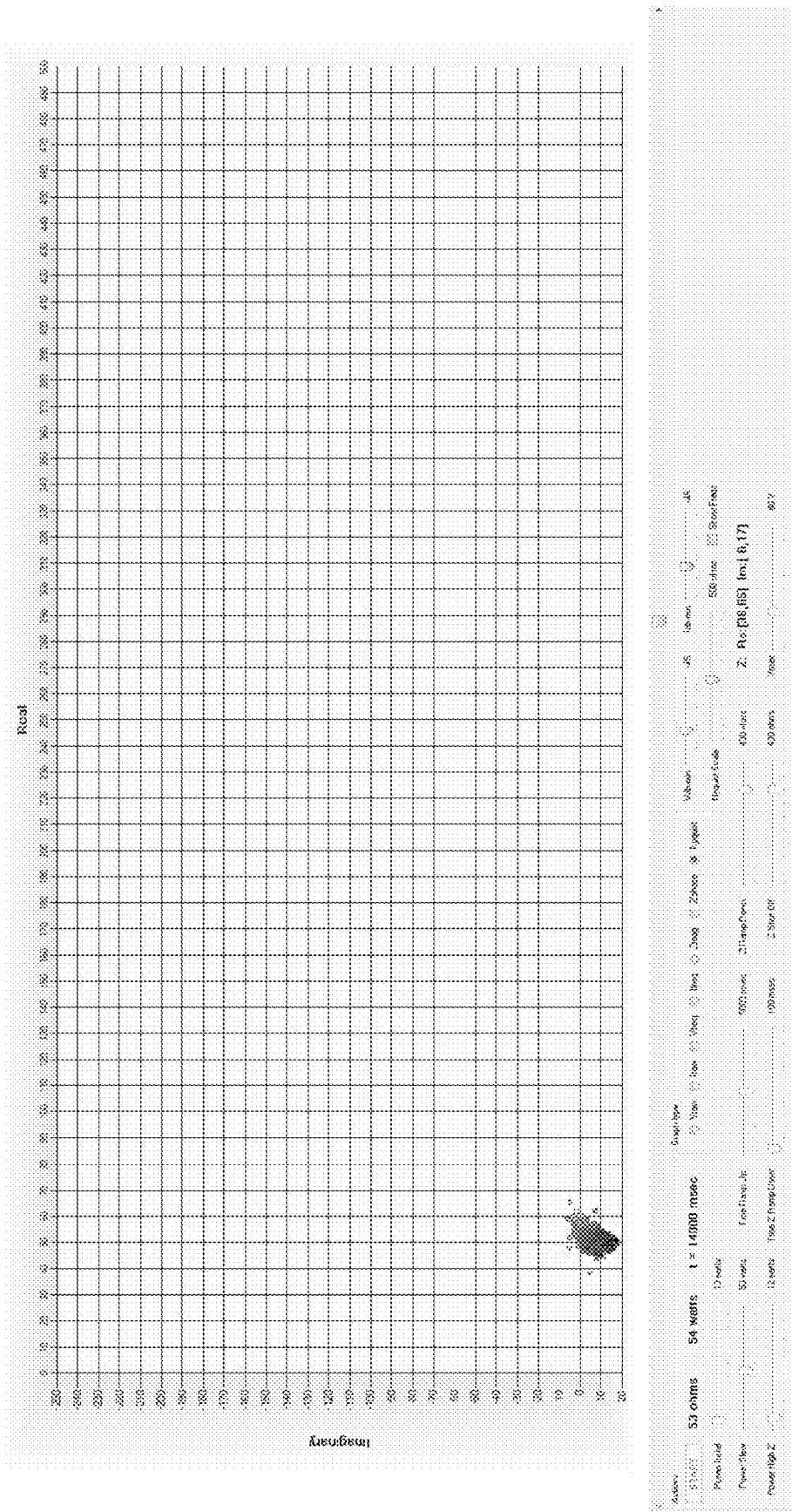
Figure 4F:
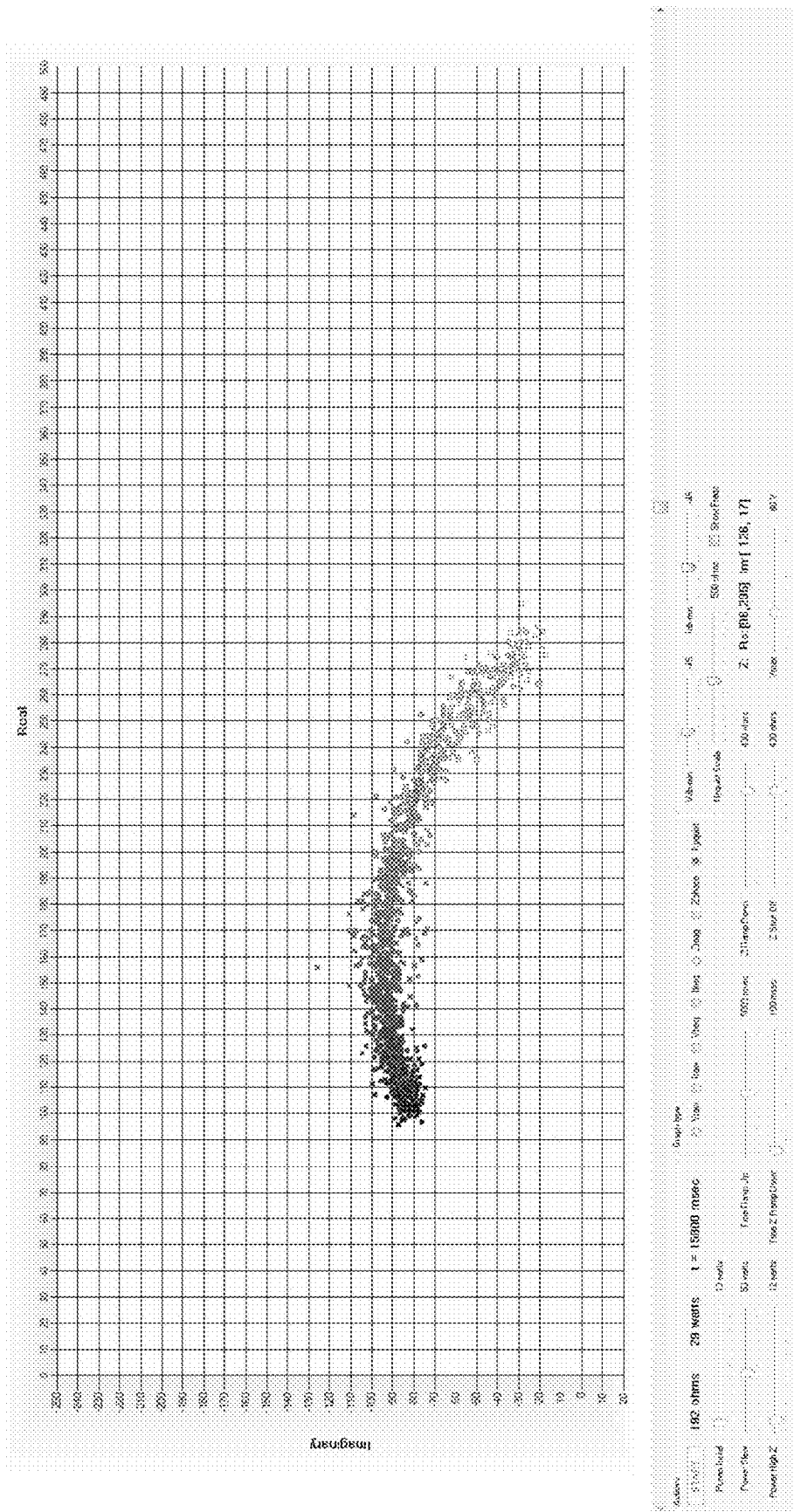
Figure 4G:
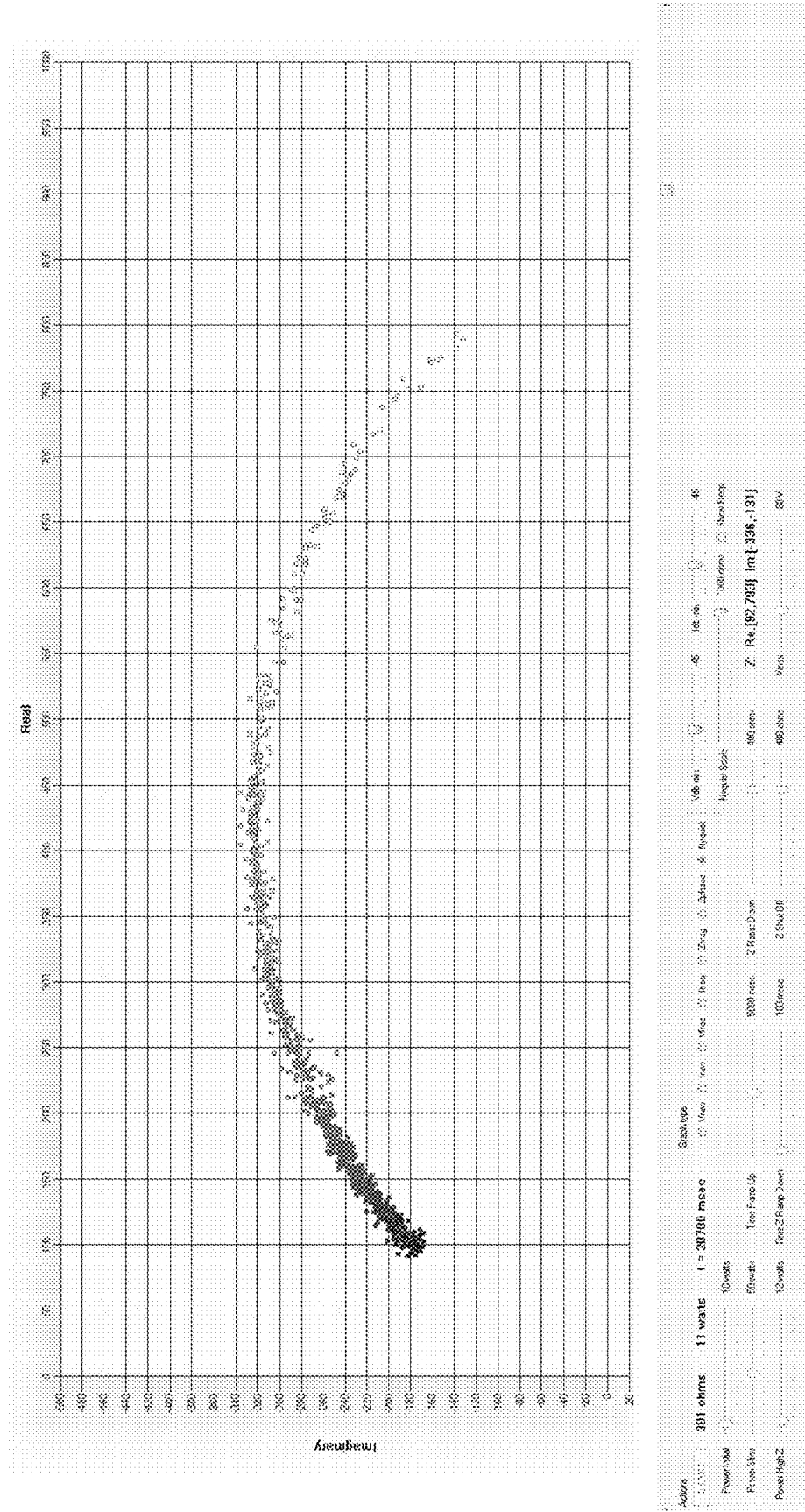

FIG. 4E, which corresponds to Stages E and F, shows substantial tissue desiccation beginning due to vaporization of water and subsequent exit of that vapor from the tissue, as evidenced by the start of pronounced changes in tissue impedance measurements. Stage E corresponds to the point at which $Z_{real}$ values begin to increase. Stage F corresponds to the point at which maximum $Z_{imag}$ values are reached. During these two stages, molecular mobility begins to decrease with increasing tissue desiccation. In FIG. 4F, which corresponds to Stage G, swiftly increasing $Z_{real}$ values and decreasing $Z_{imag}$ values indicate a rapid rate of decrease in tissue moisture, as electrically-conductive water quickly exits the tissue as vapor. At Stage G, tissue desiccation is nearly complete, and welds are "set" as molecular mobility is restricted in the dry tissue. In FIG. 4G, which corresponds to Stage H, tissue desiccation is complete, as evidenced by high $Z_{real}$ values, low $Z_{imag}$ values, and slowing in the rates of change of measured impedances. Impedance values at Stage H reflect the electrical properties of the heated, dry tissue. At this stage, in the absence of inadvertent thermal damage and of rehydration effects, the tissue weld exhibits its initial bond strength.

Figure 5:
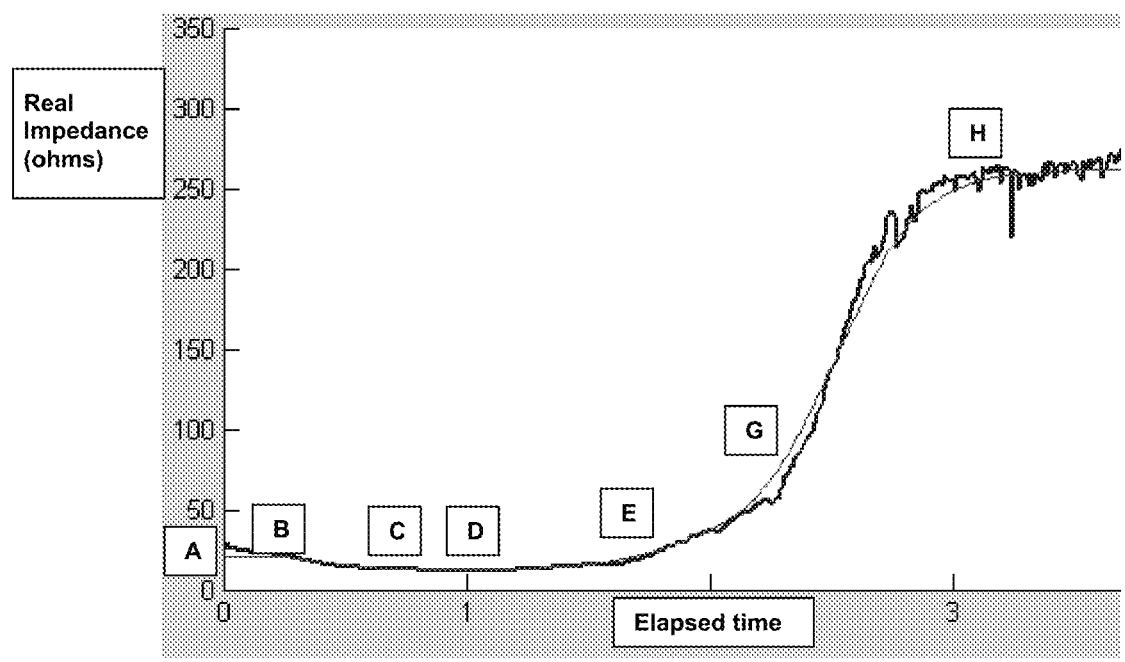
FIG. 5 is a graph of an example impedance measured in a narrow radio frequency (RF) range or single frequency by a conventional commercial system.

In contrast and referring to FIG. 5, with a conventional commercial system, the real component of impedance is measured in a narrow RF frequency range (hereinafter referred to as a "single-frequency"), which typically is concentrated at around 495 kHz or within a range of plus or minus 5% from 495 kHz, and commonly represented as a single frequency value. The temporal impedance response to energy delivery, as measured with a single-frequency system, typically follows the same weld stages as observed using BIS measurement. In Stage A, at the start of energy delivery, real impedance is nominally approximately 30-70 ohms (e.g., the initial state of naïve/untreated tissue, with impedance value depending upon amount and type of tissue). In Stage B, the real impedance decreases as tissue heats. In Stage C, the real impedance reaches its minimum value of approximately 20-30 ohms. In Stage D, real impedance dwells at this level for a period of time (e.g., the duration depends upon amount and type of tissue). In Stage E, the real impedance begins to rise, slowly and for a very brief amount of time. Stage F, in which maximum values of imaginary impedance can be determined using BIS measurement, is not applicable to conventional commercially available systems because of the absence of measurement of imaginary impedance in such systems. In Stage G, the real impedance rises rapidly, generally up to a value of several hundred ohms. In stage H, the real impedance reaches a threshold value at which energy delivery is terminated by the electrosurgical generator algorithm.

Many of the algorithms used by conventional commercial systems deliver energy at a constant power level, except in the regions in which the electrosurgical generator is current- or voltage-limited, with energy termination typically occurring at a pre-determined impedance value or at a predetermined time. Impedance measurement is typically of the real component only, ignoring the imaginary component.

Although each of the BIS weld stages A-H described herein are present during the example weld described above with respect to FIG. 5 using a single-frequency impedance measurement (i.e., the tissue undergoes the same experience of hyperthermic welding), stage detection using single-frequency measurement is considerably more difficult and less accurate than stage detection using BIS measurement due to the extremely small magnitudes of single-frequency impedance changes between Stages A through E. For example, if the single-frequency impedance measurements were graphed in the same manner as the BIS measurements shown in FIGS. 4A-G, they would appear as a single datum point for each weld stage graph. Furthermore, the majority of conventional commercial systems measure only real impedance, ignoring information provided by imaginary impedance. Moreover, unlike BIS measurement data, single-frequency data cannot be used to accurately discern between different tissue conditions, such as an amount of tissue, a moisture level of the tissue, and a type of the tissue. For example, a small, untreated blood vessel and a large segment of previously-welded, partially-desiccated tissue both have similar single-frequency temporal impedance signatures during welding, whereas the BIS temporal impedance signatures thereof are distinctly different and thus much more easily differentiated.

This inability of single-frequency measurement to precisely discern tissue conditions and weld status is a weakness of conventional commercial systems. Consequently, attempts have been made to improve the level of information available for power control algorithm decisions, by adjunctive measures such as temperature measurement at the jaws of the instrument 10, 110. Although the additional detail provided by temperature sensors can be helpful, it adds complexity and cost to the system, and still provides only an incomplete picture of the tissue conditions and weld status.

The much-increased sensitivity and specificity provided by BIS measurement are highly advantageous for informing algorithm decisions and control functions regarding energy delivery. In one implementation, systems and methods disclosed herein are configured or designed to exploit the increased levels of sensitivity and specificity with respect to instantaneous tissue condition and weld status that are provided by BIS measurement.

In an example, the power delivered to biological soft tissue during welding can be adjusted based on a rate of change of BIS measurements of real impedance. The controller 24 can compare a span of measured real impedance ($Z_{real}$, or Zreal) values at two points in time, t1 and t2, in order to compute a desired generator output power for a subsequent time point t3. Based on the calculation, the controller 24 adjusts or causes to be adjusted the power delivered to the soft tissue at time t3 to affect either an increase or decrease in the rate of change in real impedance, in order to achieve a desired optimization of weld stage, as described in more detail herein.

Upon initiating energy delivery to the tissue, output power can be continually adjusted by the controller 24 based on the following equation (1):

$$P_{t3}=([P_{t1}+P_{t2}]/2)-k_A*[\Delta Z_{t2}-\Delta_{t1}]/[\Delta_{t2}+\Delta Z_{t1}]*([P_{t1}+P_{t2}]/2) \quad (1)$$

wherein $P_{tn}$=power delivered to the biological tissue at time tn, $k_A$=scaling constant A where typically $0 \leq k_A \leq 1$, $\Delta Z_{tn}$=maximum $Z_{real}$−minimum $Z_{real}$, as measured at time tn, and time point t1 occurs before time point t2, which occurs before time point t3. The first term of the equation (1), ($[P_{t1}+P_{t2}]/2$), represents the average output power during the span of t1 to t2. This value is used as a baseline power level at time t3, to which the second term is either additive or subtractive. The second term of the equation (1), $-k_A*[\Delta Z_{t2}-\Delta Z_{t1}]/[\Delta Z_{t2}+\Delta Z_{t1}]*([P_{t1}+P_{t2}]/2)$, includes the desired power adjustment. The portion $[\Delta Z_{t2}-\Delta Z_{t1}]/[\Delta Z_{t2}+\Delta Z_{t1}]$ represents a core of the adjustment, the numerator of which is proportional to the extent of the difference between $\Delta Z_{t2}$ and $\Delta Z_{t1}$, such that larger differences result in larger adjustments, either additive or subtractive, to output power, and the denominator of which is always larger than the numerator, ensuring that the computed value of $P_{t3}$ remains positive (i.e., the second term of the equation, if subtractive, does not exceed the first term, resulting in a negative computed value for $P_{t3}$). As described herein, ($[P_{t1}+P_{t2}]/2$) represents an average power immediately preceding time t3, so that the adjustment is calculated as a fraction of this average power, which ensures that the adjustment is relevant in magnitude to the current power level. A scaling factor $k_A$ allows for either additional enhancement or dampening of the adjustment term.

Figure 6:
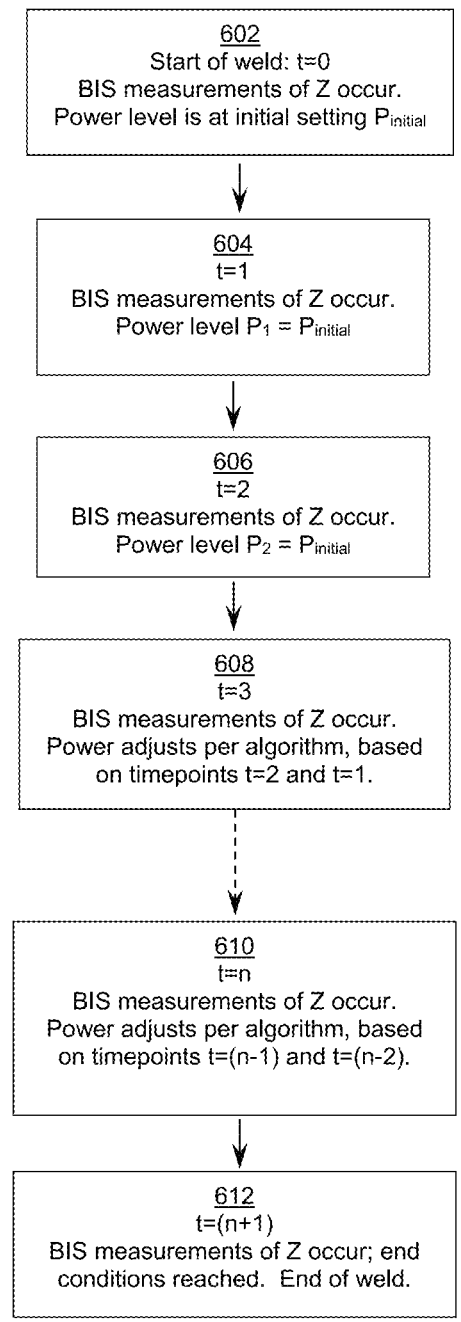
FIG. 6 is a flow chart of a method for monitoring and adjusting power delivered to soft tissue during a weld.

Referring to FIG. 6, in an example, the controller 24 can adjust output power delivered to the tissue sequentially during the weld. In scenario 602, the weld is started at an initial power level and the controller 24 begins to receive or determine BIS measurements of impedance. In scenarios 604 and 606, the BIS measurements of impedance continue to occur and the controller 24 receives or determines values for the impedance at time points t2 and t1, i.e., $\Delta Z_{t2}$ and $\Delta Z_{t1}$. For example, as the span of Zreal values ($\Delta Z_{t2}-\Delta Z_{t1}$) decreases indicating initial heating and cell membrane rupture, the controller 24, in scenario 608, can increase or cause to be increased the output power delivered to the soft tissue to minimize an amount of time in this portion of the weld (e.g., primarily Stages B and C) and thus the overall weld duration. As the span of Zreal values becomes stable between time points t1 and t2, e.g., indicating dwell, the controller 24 can minimally-adjust the output power delivered to the soft tissue in scenario 608 to extend the duration of dwell at optimal conditions for weld formation (e.g., primarily Stage D). For example, the controller 24 can control the delivery of power in Stage D based on a power adjustment algorithm that has been modified to prolong the duration of optimal tissue conditions for weld formation, specifically those of high temperature, applied pressure, and high molecular mobility. The controller 24 can control the delivery of power so that the impedance of the biological tissue, e.g., Zreal, dwells at a minimum value for the biological tissue for an extended period of time (i.e., extended with respect to a period associated with constant power algorithms). In one implementation, the controller 24 can determine when the impedance (or span of impedances) of the tissue has reached the minimum value and extend the duration of the current tissue conditions, e.g., by controlling the power delivery to the clamped tissue to maintain temperature high enough for weld formation, but without inducing substantial water vaporization and the corresponding increase in real impedance (i.e., transition into Stage E). BIS measurements of impedance continue to be received or determined by the controller 24 in scenario 610 as the soft tissue progress through the weld stages such that the power is continuously or periodically updated based on the updated impedance values, e.g., received at time points t(n-1) and t(n-2). As the span of Zreal values increases, e.g., indicating substantial tissue desiccation, the controller 24 in scenario 610 decreases output power delivered to the soft tissue to achieve greater control of the desiccation process, in order to avoid thermal degradation of the weld and surrounding tissues (e.g., primarily Stages E through H). In scenario 612, the controller 24 determines based on the BIS measurements that end conditions for the weld have been reached and terminates the output of power to the soft tissue.

It can be appreciated from equation (1) that power adjustments can be calculated from the rate and direction of impedance changes, which provide information regarding tissue condition and weld status, and as a function of the power output immediately preceding the time of adjustment, which ensures that the degree of power adjustment is relevant for the current tissue condition and weld status. Furthermore, because the power adjustment is calculated in relative rather than absolute terms, the controller 24 inherently takes into account differences in tissue type (each of which can have unique electrical characteristics) and tissue volume (e.g., thickness, amount of contact with instrument electrodes, etc.), giving the controller 24 the ability to automatically adapt to a wide variety of conditions.

In another example, the controller 24 can adjust or cause to be adjusted the power delivered to the soft tissue based on a rate of change of BIS measurements of imaginary impedances, or of real and imaginary impedances. As discussed herein, Zreal can be chosen as the parameter of interest because of its large range during the weld, large magnitude of change, and straightforward correlation between BIS measurements and tissue effects. However, the controller 24 can adjust the power delivered to the soft tissue based on a rate and direction of change of imaginary impedance values ($Z_{imag}$, or Zimag), or based on a combination of both Zreal and Zimag. Use of Zimag measurements may be useful, or in some circumstances even preferable, in order to further exploit information regarding capacitive and inductive elements of a tissue circuit. Although typically more costly with respect to computational time and power, use of both Zreal and Zimag can provide greater sensitivity and specificity regarding tissue condition and weld status, enabling the controller 24 to achieve even finer precision in tuning output power in response to tissue phenomena, in order to improve conditions for tissue welding.

In an implementation, the instantaneous span of BIS measurements of real impedances (used to calculate ΔZtn) can be replaced with the instantaneous span of BIS measurements of imaginary impedances, to achieve a similar effect with respect to adjustment of output power. Use of imaginary rather than real impedance measurements in the power adjustment calculation may be more desirable in tissues containing a higher proportion of capacitive materials (e.g., fat), or in tissues that possess a higher degree of electrical anisotropy (e.g., muscle fibers, in which impedance measurements are more highly influenced by electrode orientation with respect to the fibers). For example, upon initiating energy delivery to the tissue, output power can be continually adjusted by the controller 24 based on the following equation (2):

$$P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2) \quad (2)$$

wherein $P_{tn}$=power delivered to the biological tissue at time tn, $k_A$=scaling constant A where typically $0 \leq k_A \leq 1$, $\Delta Z_{tn}$=maximum $Z_{imag}$–minimum $Z_{imag}$, as measured at time tn, and time point t1 occurs before time point t2, which occurs before time point t3. The first term of the equation (1), $([P_{t1}+P_{t2}]/2)$, represents the average output power during the span of t1 to t2. This value is used as a baseline power level at time t3, to which the second term is either additive or subtractive. The second term of the equation (1), $-k_A*[\Delta Z_{t2}-\Delta Z_{t1}]/[\Delta Z_{t2}+\Delta Z_{t1}]*([P_{t1}+P_{t2}]/2)$, includes the desired power adjustment. The portion $[\Delta Z_{t2}-\Delta Z_{t1}]/[\Delta Z_{t2}+\Delta Z_{t1}]$ represents a core of the adjustment, the numerator of which is proportional to the extent of the difference between $\Delta Z_{t2}$ and $\Delta Z_{t1}$, such that larger differences result in larger adjustments, either additive or subtractive, to output power, and the denominator of which is always larger than the numerator, ensuring that the computed value of $P_{t3}$ remains positive (i.e., the second term of the equation, if subtractive, does not exceed the first term, resulting in a negative computed value for $P_{t3}$). As described herein, $([P_{t1}+P_{t2}]/2)$ represents an average power immediately preceding time t3, so that the adjustment is calculated as a fraction of this average power, which ensures that the adjustment is relevant in magnitude to the current power level. A scaling factor $k_A$ allows for either additional enhancement or dampening of the adjustment term.

If treating tissues that are more heterogeneous in composition (e.g., combinations of muscle, fat, and/or connective tissues), or in which composition (and thus electrical properties) is variable or unknown, a greater degree of algorithm sensitivity to tissue conditions and weld stage changes can be achieved by using a combination of both Zreal and Zimag to calculate the amount of power adjustment. In one implementation, the controller 24 can average Zreal and Zimag adjustments, e.g., based on an equal contribution from each of Zreal and Zimag, to determine a power adjustment. For example, output power can be continually adjusted by the controller 24 based on the following equation (3):

$$P_{t3}=([P_{t1}+P_{t2}]/2)-k_A*([P_{t1}+P_{t2}]/2)*0.5*([\Delta Z_{real@t2}-\Delta Z_{real@t1}]/[\Delta Z_{real@t2}+\Delta Z_{real@t1}]+[\Delta Z_{imag@t2}-\Delta Z_{imag@t1}]/[\Delta Z_{imag@t2}+\Delta Z_{imag@t1}]) \quad (3)$$

wherein $\Delta Z_{real@tn}$=maximum Zreal–minimum Zreal, as measured at time tn, and $\Delta Z_{imag@tn}$=maximum Zimag–minimum Zimag, as measured at time tn. The remainder of the variables and/or coefficients in equation (3) can be defined in the same manner as provided above for equations (1) and (2) herein.

In another implementation, the controller 24 can use a differential weighting of Zreal and Zimag adjustments to determine a power adjustment. For example, output power can be continually adjusted by the controller 24 based on the following equation (4):

$$P_{t3}=([P_{t1}+P_{t2}]/2)-k_r*([P_{t1}+P_{t2}]/2)*[\Delta Z_{real@t2}-\Delta Z_{real@t1}]/[\Delta Z_{real@t2}+\Delta Z_{real@t1}]-k_i*([P_{t1}+P_{t2}]/2)*[\Delta Z_{imag@t2}-\Delta Z_{imag@t1}]/[\Delta Z_{imag@t2}+\Delta Z_{imag@t1}] \quad (4)$$

wherein $k_r$ and $k_i$ are scaling constants for real and imaginary portions respectively, to provide differential weighting of the adjustment for each of the real and imaginary portions. The remainder of the variables and coefficients in equation (4) can be defined in the same manner as provided for equations (1), (2), and (3) herein.

Selection of each scaling constant $k_r$ and $k_i$ may be preset in the controller 24, or may be dynamically determined and modified by the controller 24 during the course of a weld based on measured values of Zreal and Zimag, such as magnitudes of instantaneous impedance span. An example of a dynamic adjustment scheme based on magnitudes of instantaneous impedance span is shown in Table 2 below.

TABLE 2

| | THEN | |
|---|---|---|
| IF | $k_r$ | $k_i$ |
| $\Delta Z_{real@tn} \geq 10$ ohms AND $|\Delta Z_{imag@tn}| \leq 10$ ohms | 1.0 | 0 |
| $\Delta Z_{real@tn} \leq 10$ ohms AND $|\Delta Z_{imag@tn}| \geq 10$ ohms | 0 | 1.0 |
| $\Delta Z_{real@tn} \geq 10$ ohms AND $|\Delta Z_{imag@tn}| \geq 10$ ohms | 0.5 | 0.5 |

In another implementation, rather than magnitudes of instantaneous impedance span, the controller 24 can use rates of change of impedance span to dynamically adjusting the scaling constants $k_r$ and $k_i$. An example of a dynamic adjustment scheme based on rates of change of impedance span is shown in Table 3 below.

TABLE 3

| | THEN | |
|---|---|---|
| IF | $k_r$ | $k_i$ |
| $(\Delta Z_{real@t2} - \Delta Z_{real@t1}) \geq 10$ ohms AND $|\Delta Z_{imag@t2} - \Delta Z_{imag@t1}| \leq 10$ ohms | 1.0 | 0 |
| $(\Delta Z_{real@t2} - \Delta Z_{real@t1}) \leq 10$ ohms AND $|\Delta Z_{imag@t2} - \Delta Z_{imag@t1}| \geq 10$ ohms | 0 | 1.0 |
| $(\Delta Z_{real@t2} - \Delta Z_{real@t1}) \geq 10$ ohms AND $|\Delta Z_{imag@t2} - \Delta Z_{imag@t1}| \geq 10$ ohms | 0.5 | 0.5 |

In an example, the controller 24 can target the power adjustment to specific weld stages. For example, in order to simplify power delivery, or to optimize the balance of weld duration versus weld quality, or to achieve other specific effects, the controller 24 can adjust or cause to be adjusted the power output delivered to the soft tissue based on the BIS measurements for select weld stages only, while allowing the remainder of the weld (e.g., the unselected weld stages) to be completed using a conventional/generic algorithm for controlling the power delivered to the tissue. The controller 24 can be configured to detect (calculate) stage transitions based on the BIS measurements as described herein, and change the power delivery accordingly (e.g., by switching between dynamically-responding BIS algorithms and/or conventional/single-frequency algorithms/narrow-band frequency algorithms).

For example, in one implementation the controller 24 can be configured to deliberately prolong a duration of optimum conditions for weld strength formation (e.g., Stage D, high temperature and high liquid-phase moisture content in the clamped tissue) by decreasing output power during Stage D to prolong optimum weld formation conditions without inducing transition to Stage E, or by using a power adjustment formula that has been specifically optimized for Stage D, and/or by using another control process disclosed herein. The controller 24 can determine that the tissue is in Stage D based on the BIS measurements (e.g., when the spans of real and imaginary impedance values have reached minimum values, or when the arc of real and imaginary impedance values across the measurement frequency range is substantially similar to that shown in FIG. 4D), and adjust the power output to prolong the time that the tissue spends in Stage D during the weld. For example, the controller 24 can compare the BIS measurements (e.g., the span of Z values ($\Delta Z_{t2}-\Delta Z_{t1}$)) to a threshold or threshold range to determine the current weld stage of the tissue, and provide more finite power adjustment and/or overall lower temperatures to the tissue (e.g., to avoid tissue desiccation) based on the BIS measurements to extend the time that the tissue spends in Stage D during the weld. In one implementation, the controller 24 can determine when the impedance (or span of impedances) of the tissue has reached the minimum value, which indicates optimum conditions for weld strength formation, and extend the duration of the current tissue conditions, e.g., by controlling the power delivery to prolong the optimum conditions. For example, the controller 24 can limit the power delivery to the tissue to avoid heating the tissue too quickly, which can cause water vaporization and a premature loss of the optimum conditions for weld formation. In an example as discussed below with respect to equation (6), the controller can modify one or more scaling constants of a power adjustment algorithm used to calculate the power delivery based on the impedance measurement of the tissue to achieve a desired decrease in the power adjustment calculation, e.g., a 10-25% decrease, to achieve a corresponding extension in the duration of optimum tissue conditions for weld formation. The controller 24 can perform calculations to balance conflicting constraints, such as greater weld strength or improved weld consistency, versus weld time, degree of tissue desiccation (which can lead to adhesion to the instrument electrodes), extent of lateral thermal spread, etc., to adjust the power delivery to the tissue in a manner that improves or optimizes a time period that the tissue conditions remain in the optimum range.

In another implementation, for tissue that is more easily welded (e.g., tissue that more quickly develops adequate weld strength), the controller 24 can be configured to implement the power adjustment based on the BIS measurements during Stages A and B to minimize the time for the tissue to reach denaturation temperatures (e.g., to minimize overall weld duration). The controller 24 can be configured to more quickly increase the temperature and/or a level of the power delivered to the tissue during Stages A and B, or to provide a higher maximum level of the power delivered to the tissue during Stages A and B. For example, output power can be continually adjusted by the controller 24 during the particular weld stage(s) based on the following equation (5):

IF [minimum Zreal has not been reached]

THEN $P_{t3}=1.25*([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ ELSE $P_{t3}=([P_{t1}+P_{t2}]/2)-k_A*[\Delta Z_{t2}-\Delta Z_{t1}]/[\Delta Z_{t2}+\Delta Z_{t1}]*([P_{t1}+P_{t2}]/2)$ (5)

wherein the variables and coefficients in equation (5) can be defined in the same manner as provided for equations (1)-(4) herein. It is noted that the first term of the power adjustment calculation is increased by 25% from 1.0 in equation (5); however, example embodiments are not limited thereto and this term can be increased by another percentage to achieve any desired increase in the power adjustment calculation to achieve a corresponding reduction in the duration of the particular weld stage(s) by balancing conflicting constraints, such as greater weld strength or improved weld consistency, versus weld time, degree of tissue desiccation (which can lead to adhesion to the instrument electrodes), extent of lateral thermal spread, etc.

After minimizing the time spend in Stages A and B, the controller 24 can change the power adjustment when entry into Stage C or D is detected (e.g., when conditions shown in FIG. 4C or D are detected) to prolong the duration of optimum conditions for weld strength formation, or to achieve other specific effects. In one implementation, at specific stages of the weld, such as during substantial liquid-to-gas phase change and desiccation (e.g., Stages E through H), the tissue is more prone to inadvertent thermally-induced damage from high output power, and the controller 24 can be configured to implement the power adjustment to provide a greater degree of control, thereby minimizing the risk of damage to the weld (e.g., development of char, which can lead to an electrical short circuit through the weld, or formation of pockets of steam that may rupture through the weld or adjacent tissues). For example, output power can be continually adjusted by the controller 24 based on an equation that has been modified to be more sensitive to changes in the BIS measurement.

In another implementation, the controller 24 can be configured to select a power adjustment algorithm or tailor the power adjustment to a particular weld stage of the tissue. The controller 24 can be configured to implement different BIS measurement based control or algorithms for controlling or adjusting the power delivered to the tissue for one or more of the weld stages of the tissue. For example, the controller 24 can implement a different, stage-specific, BIS algorithm for each weld stage (e.g., Stages A-H described herein), which enables the controller 24 to control power delivery to the tissue based on a BIS algorithm that has been optimized for the specific weld stage. For example, as described above, the controller 24 can be configured to adjust power delivery during Stage D based on an algorithm that is configured to deliberately prolong a duration of optimum conditions for weld strength formation by decreasing output power during Stage D to prolong optimum weld formation conditions without inducing transition to Stage E. For example, output power can be continually adjusted by the controller 24 during the particular weld stage(s) based on the following equation (6):

IF [$\Delta Z_{real@m}$=minimum value of Zreal]

OR ([minimum Zreal has been reached] AND [$\Delta Z_{real@m}$≤120% of minimum Zreal])

THEN $P_{t3}=0.9*([P_{t1}+P_{t2}]/2)-k_A*[\Delta Z_{t2}-\Delta_{t1}]/[\Delta Z_{t2}+\Delta Z_{t1}]*([P_{t1}+P_{t2}]/2)$ ELSE $P_{t3}=([P_{t1}+P_{t2}]/2)-k_A*[\Delta Z_{t2}-\Delta_{t1}]/[\Delta Z_{t2}+\Delta Z_{t1}]*([P_{t1}+P_{t2}]/2)$ (6)

wherein the variables and coefficients in equation (6) can be defined in the same manner as provided for equations (1)-(4) herein. It is noted that the first term of the power adjustment calculation is decreased by 10% from 1.0, i.e., is 0.9, in equation (6); however, example embodiments are not limited thereto and this term can be decreased by another percentage to achieve any desired decrease in the power adjustment calculation to achieve a corresponding extension in the duration of the particular weld stage(s) by balancing conflicting constraints, such as greater weld strength or improved weld consistency, versus weld time, degree of tissue desiccation (which can lead to adhesion to the instrument electrodes), extent of lateral thermal spread, etc.

As can be seen from equation (6), once Stage C of the weld is reached (i.e., initial heating and cell membrane rupture are substantially complete and there is no further decrease in low frequency measurements of Zreal), the baseline output power in the first term of the power adjustment calculation is continually scaled down by a factor of 10%, so that the resulting value of Pt3 is continually reduced during weld Stages D through F, to extend the duration of optimal conditions for weld formation.

At specific stages of the weld, such as during substantial liquid-to-gas phase change and desiccation (e.g., Stages E through H), the tissue is more prone to inadvertent thermally-induced damage from high output power. The controller 24 can be programmed or configured to decrease output power during Stages G through H by continually decreasing the first term of the power adjustment calculation, e.g., by 25%, to reduce the likelihood of inadvertent thermally-induced damage from high output power. For example, output power can be continually adjusted by the controller 24 during the particular weld stage(s) based on the following equation (7):

IF ([minimum Zreal has been reached] AND
   [$\Delta Z_{real@m} \geq 120\%$ of minimum Zreal])

THEN $P_{t3} = 0.75*([P_{t1}+P_{t2}]/2) - k_A*[\Delta Z_{t2}-\Delta Z_{t1}]/[\Delta Z_{t2}+\Delta Z_{t1}]*([P_{t1}+P_{t2}]/2)$ ELSE $P_{t3} = ([P_{t1}+P_{t2}]/2) - k_A*[\Delta Z_{t2}-\Delta Z_{t1}]/[\Delta Z_{t2}+\Delta Z_{t1}]*([P_{t1}+P_{t2}]/2)$ (7)

wherein the variables and coefficients in equation (7) can be defined in the same manner as provided for equations (1)-(4) herein.

In another implementation, the controller 24 can be configured to dynamically adjust or cause to be adjusted the power adjustment algorithm used to control the power delivery to the tissue based on the BIS measurements. For example, the controller 24 can determine real-time adjustments or modifications to the power output from the generator 20 based on the BIS measurements, including Zimag or a combination of Zreal and Zimag, in order to improve weld performance by implementing a dynamic power adjustment algorithm with parameters that can be changed in real-time based on the BIS measurements. For example, optimum parameters for welding or ablating a large volume of tissue, such as organ parenchyma, may be different than optimum parameters for welding a small blood vessel, and the ability to accurately distinguish between tissue types and conditions and to dynamically adjust parameters of the power adjustment algorithm used to control the power delivery to the tissue to parameters better suited for the current tissue type and condition is highly desirable.

With a conventional commercial system, the information available to differentiate between tissue types and conditions is limited to single-frequency real impedance measurements, which typically do not provide sufficient resolution to accurately distinguish between different tissue types and conditions. In contrast, by using the characteristic BIS real and/or imaginary impedance signatures of the tissue at different stages of the weld, a much more accurate determination can be made, and the parameters of the power adjustment algorithm can be dynamically adjusted based on the determined tissue type and/or condition. These characteristic impedance signatures may include instantaneous BIS measurements, i.e., an impedance profile at a single or instantaneous point in time, and temporal changes in BIS measurements, i.e., impedance rates of change, or relative changes. For example, parameters of the power adjustment algorithm used to calculate the power delivery can be dynamically adjusted or modified by the controller 24 with respect to a time threshold to reach a minimum Zreal based on the following equation (8):

IF [minimum Zreal has been reached]

AND [amount of time to reach minimum
   Zreal$>t_{vessel-reach}$]

THEN change to large-tissue-volume parameters for
   power adjustment algorithm

ELSE continue with vessel parameters for power
   adjustment algorithm (8)

wherein $t_{vessel-reach}$=upper limit for the amount of time to reach minimum Zreal for vessels and small tissue bundles.

In another example, the parameters of the power adjustment algorithm used to calculate the power delivery can be dynamically adjusted or modified by the controller 24 with respect to a time threshold for a duration of dwell at a minimum Zreal based on the following equation (9):

IF [minimum Zreal has been reached]

AND [amount of time below ($k_T*$minimum Zreal)
   $>t_{vessel-dwell}$]

THEN change to large-tissue-volume parameters for
   power adjustment algorithm

ELSE continue with vessel parameters for power
   adjustment algorithm (9)

wherein $t_{vessel-dwell}$=upper limit for amount of time during which impedance dwells at or near minimum Zreal, and $k_T$=scaling constant T, typically with $1.05 \leq k_T \leq 1.15$.

Values for $t_{vessel-reach}$ and $t_{vessel-dwell}$ can be determined based on factors including instrument electrode design, e.g., the electrode design of the forceps 10 or laparoscopic tool 110, baseline output power level of the instrument 10, 110 or generator 20, and/or particular requirements of the procedures under consideration, e.g., cutting, coagulating, dissecting, welding, sealing, ablation, etc.

In some examples, the controller 24 can be configured to modify or cause to be modified a timing of each power adjustment to be earlier or later, e.g., by modifying the generator power control feedback loop, to change a degree of responsiveness of the power adjustment system or method to a current tissue condition and weld status. For example, if the generator 20 measures impedance every 100 ms, and requires 50 ms of each 100 ms cycle to collect data, perform a calculation, and transmit updated power level information to the RF output stage 28, the timing of implementation of the updated power level will affect the degree of responsiveness of power adjustment to changing tissue conditions. Immediate implementation provides the highest degree of responsiveness, while delaying implementation until later in the remainder of the measurement cycle decreases responsiveness. In other implementations, the length of the measurement cycle can be shortened or lengthened, or implementation of the updated power level can be delayed to a subsequent measurement cycle, with the same overall outcome of changing degree of responsiveness. Specific events during the weld, such as during substantial transition of water within the tissue from liquid to vapor phase, and final desiccation of the tissue, are associated with rapidly-changing tissue conditions (and corresponding impedance values). The ability of the generator 20 to adjust output power quickly in response to these rapid changes minimizes the risk of undesirable effects such as rupture of pockets of steam through the tissue or development of char; however, rapidity of response should be moderated to achieve a balance with conflicting constraints such as overall weld duration, tissue adhesion to electrodes, and lateral thermal damage. These techniques for modifying the timing of the power adjustment can be used as alternatives (or additions) to adjusting the scaling factor $k_4$.

In another example, a working envelope controller 24 can be programmed or configured such that BIS measurements or calculations outside of the working envelope are not implemented or used to determine the power adjustment (e.g., minimum and/or maximum power levels beyond which BIS adjustments need not be measured and used by the power adjustment, or a minimum value of BIS $\Delta Z$ for power adjustment to be implemented, etc.). For example, the controller 24 can adjust or cause to be adjusted the power delivered to the tissue based only on BIS measurements that satisfy a threshold or threshold range. The techniques in this example can be used not only to modulate the responsiveness of the controller for the same purposes as previously described, but also as a method of correcting for noise in the impedance measurements.

In another implementation, the controller 24 can derive the BIS measurement based power adjustments from predetermined look-up tables instead of performing real-time calculations, which requires less computational time and power. For example, the controller 24 can adjust the power delivered to the tissue based on a value or range of values associated with the BIS measurement, such as the span of Z values ($\Delta Zt2-\Delta Zt1$), defined in a look-up table.

In some implementations, the controller 24 can be programmed or configured to adjust or cause to be adjusted the power delivered to the tissue based on BIS $\Delta Z$ measurements from a more limited set of predetermined frequencies (e.g., 2 MHz, 1.5 MHz, 1 MHz, 750 kHz, 500 kHz, 250 kHz, and 0 Hz, rather a larger range, such as 0 Hz through 10 MHz at 1.25 kHz intervals). The frequency set (i.e., the number of frequencies and the specific frequencies) may be selected such that the characteristic BIS impedance signature shown in FIGS. 4A-G can be easily discernible. A further benefit of using only selected frequencies is the avoidance of frequency ranges in which inaccuracies and/or undesirable effects may be observed, such as anisotropic measurement variability at alpha dispersion frequencies, or inadvertent nerve or muscle stimulation at lower frequencies. A controller 24 that is configured to use a more limited set of frequencies to perform tissue monitoring and power adjustment requires less measurement and computational time and less power than a controller 24 configured to use more comprehensive scan, and can greatly reduce file size if data are to be stored. In one implementation, the controller 24 can be programmed or configured to bin BIS $\Delta Z$ measurements based on frequency to create a more limited set of frequencies. For example, the bin size can be selected based on a type of tissue to be welded and/or a type of test to be performed, and BIS $\Delta Z$ measurements that fall within the same range of frequencies are binned together. The controller 24 can be programmed or configured to adjust the power delivered to the tissue based on only the frequencies of each bin, rather than each of the individual $\Delta Z$ measurements. In another implementation, the controller 24 can be programmed or configured to receive or determine measurements at only a certain number of discrete waveforms to create a more limited set of frequencies.

In another implementation, the controller 24 can determine a weld endpoint and/or an error condition based on the BIS measurements. In conventional commercial systems, data obtained via a single-frequency impedance measurement are used to determine a weld endpoint, i.e., a time point for shut off of power delivery to the tissue. The single-frequency impedance is typically compared with a predetermined value, such as a threshold value, at which output power to the instrument electrodes is shut off. Alternatively, changes in single-frequency impedance values may be compared to predetermined criteria, such as rates or magnitudes of change, above which the power delivery to the tissue is shut off. These methods are limited at least because the value of the single-frequency impedance measurement used to make the weld endpoint determination reflects a combination of tissue characteristics such as thickness, contact area with the electrodes, type (e.g., composition), and remaining water content, none of which can be individually discerned from the measurement.

The controller 24 can be programmed or configured to use BIS measurements to more accurately determine tissue characteristics, such as water content. For example, when tissue desiccates during welding, the molecular mobility needed for weld formation becomes limited, which results in additional energy delivery to the tissue having minimal effect in terms of increasing weld strength. Further, the additional energy delivery to the tissue may have the undesired consequence of causing thermal damage to the weld and to adjacent tissues. Unlike the conventional commercial systems described above, tissue desiccation, as well as the period preceding desiccation, are more easily detected from the BIS measurement data as a marked widening of the spans of both real and imaginary impedances (Stages G and H). A magnitude of impedance changes from Stages E-F through to Stage H, such as the substantial expansion of range of Zreal, is a more discernible and accurate indicator of tissue condition than a single-frequency impedance measurement. As shown in FIG. 4G, at Stage H of a tissue weld, the BIS measurement appears as a large arc of real and imaginary impedance values across the measurement frequency range, whereas the single-frequency measurement consists of a single impedance datum point. At this point in the welding process, the spread in BIS measurements clearly indicates tissue desiccation (i.e., completion) of the weld in question, whereas this determination cannot be definitively made from the single value of the single-frequency impedance measurement, because the single-frequency impedance value at weld completion may differ with tissue type or quantity. In contrast to conventional commercial systems, systems and methods according to example embodiments that utilize BIS measurements provide evidence that is more indicative for algorithm decision-making, and more accurate in terms of sensitivity and specificity to tissue conditions.

Similarly, BIS measurements and information can enable improved identification of error conditions, such as power being delivered to the tissue after the tissue is fully desiccated.

For example, the controller 24 can be programmed or configured to determine a weld end point or error condition with respect to Zreal and to control the generator power output to terminate based on the following equation (10):

IF ([minimum Zreal has been reached] AND
    [$\Delta Z_{real@tn} \geq 400$ ohms])

THEN terminate generator power output to instrument     (10)

In another example, the controller 24 can be programmed or configured to determine a weld end point or error condition with respect to Zimag and to control the generator power output to terminate based on the following equation (11):

IF ([maximum Zimag has been reached] AND
    [$\Delta Z_{imag@tn} \geq 200$ ohms])

THEN terminate generator power output to instrument     (11)

In one example, the controller 24 can be programmed or configured to determine a weld end point or error condition with respect to Zreal and Zimag and to control the generator power output to terminate based on the following equation (12):

IF (([minimum Zreal has been reached] AND
    [$\Delta Z_{real@tn} \geq 400$ ohms]) OR ([maximum Zimag
    has been reached] AND [$\Delta Z_{imag@tn} \geq 200$
    ohms]))

THEN terminate generator power output to instrument     (12)

In another implementation, the controller 24 can be programmed or configured to determine a weld end point or error condition with respect to Zreal and Zimag and to control the generator power output to terminate based on the following equation (13):

IF (([minimum Zreal has been reached] AND
    [$\Delta Z_{real@tn} \geq 400$ ohms]) AND ([maximum Zimag
    has been reached] AND [$\Delta Z_{imag@tn} \geq 200$
    ohms]))

THEN terminate generator power output to instrument     (13)

For equations (10), (11), (12), and (13), $\Delta Z_{real@tn}$=maximum Zreal−minimum Zreal, as measured at time tn, and $\Delta Z_{imag@tn}$=maximum Zimag−minimum Zimag, as measured at time tn. Although described herein with respect to threshold values of 400 ohms for $\Delta Z_{real@tn}$ and 200 ohms for $\Delta Z_{imag@tn}$, disclosed embodiments are not limited thereto and the threshold values used in equations (10), (11), (12), and (13) may be adjusted or modified based on tissue types and conditions and a particular application or procedure.

In another example, the controller 24 can be programmed or configured to use the BIS measurement for tissue identification. Although some disclosed embodiments described herein implement the BIS measurement with respect to temporal changes, the controller 24 can be programmed or configured to adjust the power delivered to the target tissue based on frequency-dependent real and/or imaginary impedance spectra as measured at a single or instantaneous point in time. The electrical behavior of tissue constituents has been explored at great depth for the purposes of collecting information regarding tissue type (e.g., muscle or fat; normal, ischemic, or infarcted; normal or cancerous). The impedances of various biological tissues across a wide range of frequencies (e.g., 10 Hz to 10 MHz) can be measured and stored, for example, in a database or lookup table, for future reference or comparison. The controller 24 can compare measurements of impedance spectra at a single time point for the target tissue to the stored measurements of the various biological tissues to determine the composition of the target tissue and/or an appropriate power adjustment algorithm for controlling the supply of power to the target tissue for treatment. For example, the controller 24 can be programmed or configured to compare an instantaneous impedance spectra to known characteristic electrical properties of a plurality of different tissue types to determine a tissue type of the plurality of various different tissue types that corresponds to the target tissue, and the controller 24 can switch (or be caused to switch) between a plurality of pre-configured power adjustment algorithms tailored for each different tissue type based on the tissue type determined to correspond to the target tissue. In another implementation, the controller 24 can be programmed or configured to measure instantaneous impedance spectra periodically during the course of energy delivery, and to switch (or cause to be switched) between a plurality of pre-configured algorithms based on each instantaneous set of impedance spectra measurements. Although less informative with respect to tissue response than power adjustment algorithms based on temporal changes in impedance spectra, the use of instantaneous impedance measurements requires less computational time and power, and can greatly reduce file size if data are to be stored.

Further elucidation can be achieved when initial-/naïve-state BIS measurements are used in combination with temporal BIS impedance response upon application of energy. Initial impedance (Z) values, the duration of weld stages, and the extent of Z change between weld stages, can be used to more accurately determine tissue type, tissue status, and an amount of tissue in the jaws of the instrument 10. For example, the controller 24 can be programmed or configured to compare an initial Z to the known characteristic electrical properties of different tissue types and monitor the temporal response of Z to energy delivery to determine the type of tissue. With such information the controller can switch (or be caused to switch) between a plurality of pre-configured algorithms. The controller 24 can be programmed or configured to monitor initial Z values and a duration and extent of Z change from weld Stage A to Stage C to determine a tissue status. For example, low initial Zreal and near-zero initial Zimag values, in combination with minimal Z change from Stage A to Stage C, is indicative of ruptured cell membranes and high (normal) overall moisture content, as in the case of prior thermal treatment without substantial desiccation. In contrast, high initial Z values with minimal Z change from Stage A to Stage C is suggestive of low moisture level, as in the case of prior desiccation. The controller 24 can be programmed or configured to monitor initial Z, the extent of Z change from Stage A to Stage C, the amount of time required to reach Stage C, and the duration of Stage D to determine the amount of tissue between the jaws of the instrument 10, 110. Although the latter is most indicative of amount of tissue, the first three listed parameters are sufficient to accurately estimate tissue quantity.

Disclosed embodiments are described herein primarily with respect to the welding of soft tissues. However, BIS measurements have utility in numerous medical applications beyond tissue welding, such as for ablation of tissues to treat cardiac electrophysiological disorders or to necrose tumor masses, or for any other energy delivery applications that induce cellular-level structural or compositional changes in tissue.

Figure 7:
FIG. 7 is a perspective view of a bipolar RF epicardial clamp device.

For example, in an epicardial ablation system 710 configured with clamping jaws/electrodes 712, as shown in FIG. 7, the controller 24 can be programmed or configured to use BIS measurements in a same or a similar manner as previously described herein for tissue welding, e.g., with respect to electrosurgical instrument 10, 110, in order to quickly bring tissue up to therapeutic temperature, thereby shortening power application time. The epicardial ablation system 710 including the jaws/electrodes 712 may be connected to the generator 20 in a same or similar manner as the electrosurgical device 10, 110 described herein with respect to FIG. 1A, i.e., through cable 18, which includes the supply and return lines 4, 8 coupled to the active and return terminals 30, 32, respectively (FIG. 1B). The RF output stage 28 is configured to generate a waveform for performing BIS measurements (e.g., by the sensor circuitry 22).

The controller 24 can continuously monitor the BIS measurements throughout a course of energy delivery for indications or evidence of atypical impedance changes, such as a premature, abrupt, or otherwise unexpected increase in real impedance values, which can indicate the formation of macroscopic pockets of water vapor within the tissue. The controller 24 can adjust or cause to be adjusted the power adjustment algorithm based on a determination or detection of an atypical impedance change, e.g., to immediately reduce the power delivered to the tissue to avoid tissue rupture. For example, if the impedance measurement or a rate of change of the impedance measurement violates a threshold value for the impedance measurement at a particular time, the controller 24 can determine an atypical impedance change and adjust or cause to be adjusted the power adjustment algorithm to reduce the power delivered to the tissue. In some implementations, the controller 24 can use BIS measurements as previously described herein with respect to tissue welding to determine ablation endpoints, in order to shorten application time, to avoid excessive damage to the treated tissue, and to minimize the potential for endocardial thrombus formation in the vicinity of the treated tissue from excessive or prolonged heating. The increased sensitivity and specificity of BIS measurements in comparison with conventional single-frequency RF systems enhance the safety, effectiveness, and efficiency of tissue ablation procedures.

Figure 8A:
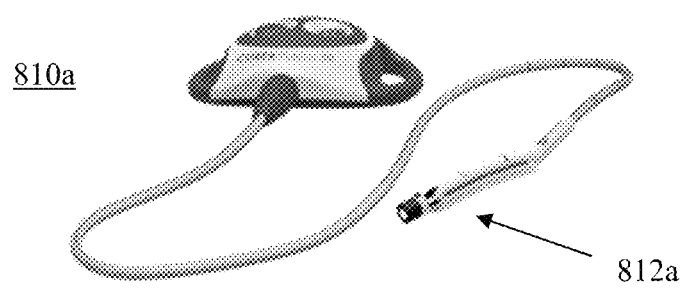
FIG. 8A is perspective view of a RF epicardial ablation device.
Figure 8B:
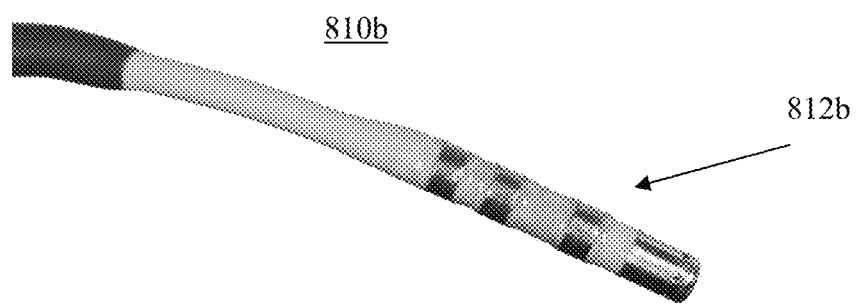
FIG. 8B is a perspective view of a distal end of a RF endocardial ablation catheter.

In another example, electrodes 812a or 812b of a cardiac ablation system 810a or 810b, as shown in FIGS. 8A and 8B, can be placed in contact with either the epicardial surface (electrodes 812a in FIG. 8A) or endocardial surface (electrodes 812b in FIG. 8B) of the heart to deliver energy to the tissue and measure impedance, and BIS measurements therefrom can be collected and used by the controller 24 in the same or similar manner as described herein with respect to the epicardial ablation system 710 as shown in FIG. 7, or with respect to electrosurgical instrument 10, 110, to address the same or similar clinical considerations, e.g., reduction of power application time, determination of ablation endpoint, avoidance of tissue rupture or excessive damage, and minimization of endocardial thrombus potential, and to achieve the same or similar procedural advantages.

Figure 9:
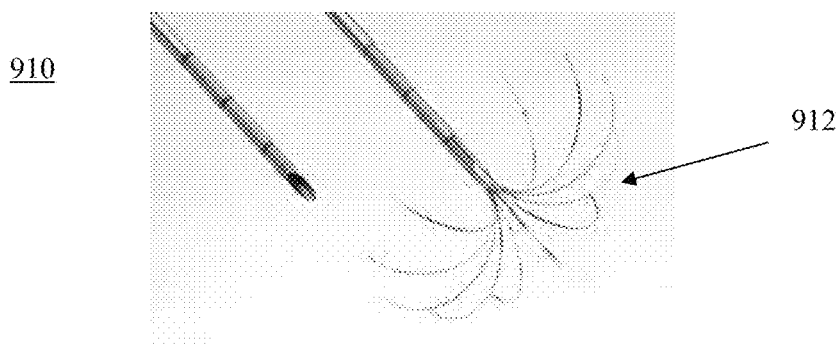
FIG. 9 is a perspective view of a soft tissue ablation device.

In one example, disclosed embodiments can be implemented in a tumor ablation system. For example, electrodes 912 of a soft tissue ablation device 910 as shown in FIG. 9, shown with the electrodes 910 retracted in the left side of FIG. 9 and the electrodes 912 extended in the right side of FIG. 9, can be placed in contact with tissue to deliver energy to the tissue and measure impedance, and the controller 24 can use the BIS measurements in a same or similar manner as described herein with respect to the epicardial ablation system 710 as shown in FIG. 7, or with respect to electrosurgical instrument 10, 110, to perform tissue identification and to guide selection of an appropriate power delivery algorithm for the tissue type, and rates of change of BIS measurements can be used to extrapolate the volume of ablated tissue, e.g., by comparing $\Delta Z$ with predetermined empirical data for each of a plurality of known tissue types.

Systems and methods for tissue monitoring and power delivery adjustment as disclosed herein can use any algorithm-based control or adjustment that is based on instantaneous broadband impedance spectroscopy measurements, or on temporal changes in broadband impedance spectroscopy measurements, in order to optimize specific aspects of the weld or ablation, or of the welding or ablation processes, for example, by optimizing the balance between a set of conflicting constraints: e.g., greater weld strength or improved weld consistency or improved ablation safety, versus weld or ablation time, degree of tissue desiccation (which can lead to adhesion to the instrument electrodes), extent of lateral thermal spread, etc. Depending upon the unique requirements of various applications of example embodiments, different tradeoffs may be made for the purposes of optimization.

Figure 10:
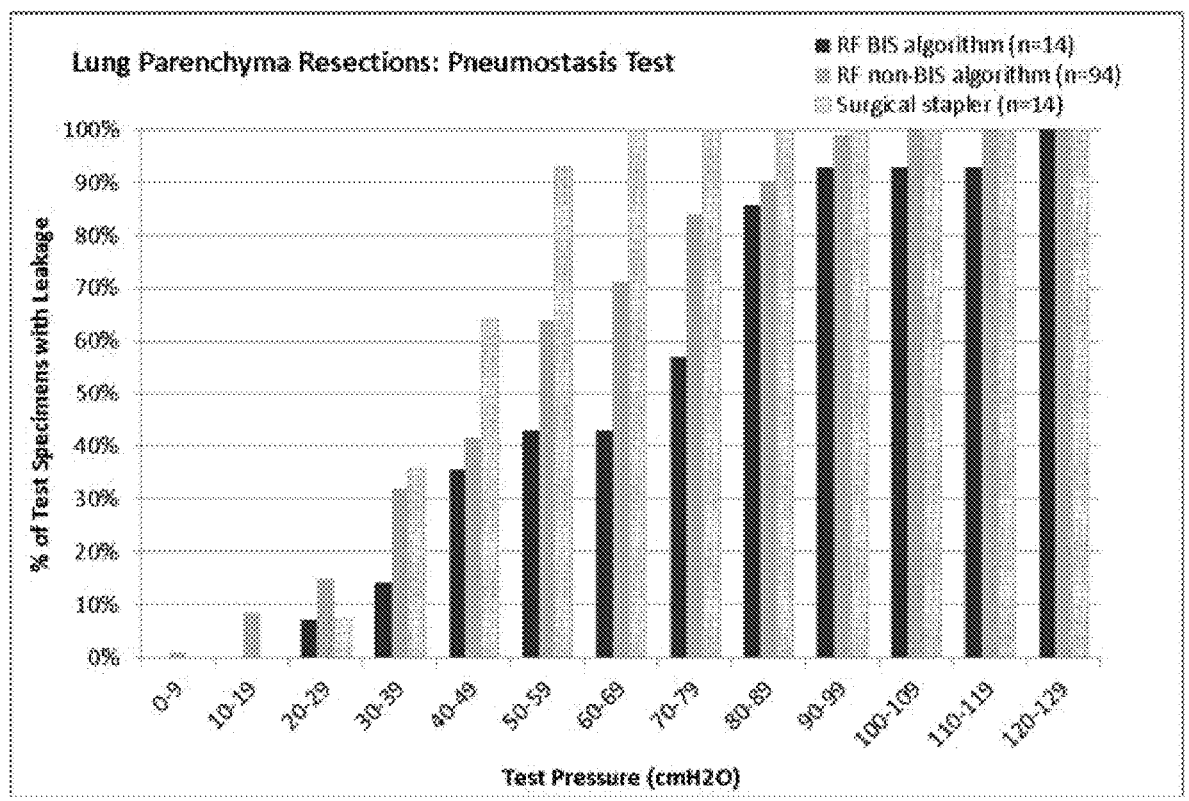
FIG. 10 is a graph comparing an example RF broadband impedance spectroscopy (BIS) system to both a conventional RF non-BIS system and a conventional commercial surgical stapler.

FIG. 10 is a graph comparing an example RF broadband impedance spectroscopy (BIS) based weld system to both a conventional RF non-BIS weld system and a conventional commercial surgical stapler. Each of the systems were tested based on a leakage pressure evaluation for welds created in pulmonary parenchyma. For the leakage tests, resection lines were pressurized with increasing pressure, until leakage was detected at the resection line, the results of which are shown in FIG. 10. For example, as shown in FIG. 10, the RF BIS-based weld system significantly outperforms both the conventional RF non-BIS weld system, demonstrating the greatly increased efficacy of BIS-based power adjustment with respect to tissue weld strength, and the conventional commercial surgical stapler, which represent the current clinical standard of care for pulmonary resection devices.

While various results were achieved with respect to pulmonary parenchyma, the principles and solutions as described and claimed may also be applied to other tissue types including for instance such tissues as bowel tissue, the appendages of the heart such as the left-atrial appendage, pancreatic tissue, and liver tissue.

The embodiments have been described with reference to various examples. Modifications and alterations will occur to others upon reading and understanding the foregoing examples. Accordingly, the foregoing examples are not to be construed as limiting the disclosure.

What is claimed is:

1. A biological tissue monitoring system comprising:
control circuitry programmed or configured to monitor an impedance of biological tissue during electrosurgical welding of the biological tissue, wherein the control circuitry is programmed or configured to:
receive or determine an impedance measurement of the biological tissue in response to a power delivered to the biological tissue at a plurality of frequencies and a plurality of time points, wherein the impedance measurement comprises real impedance and imaginary impedance;

adjust or cause to be adjusted the power delivered to the biological tissue at a subsequent time point based on the impedance measurement at the plurality of frequencies and the plurality of time points;

determine based on the impedance measurement at the plurality of frequencies and the plurality of time points a current weld stage of the biological tissue; and adjust or cause to be adjusted the power delivered to the biological tissue at the subsequent time point based on the current weld stage of the biological tissue;

wherein the current weld stage includes a first stage in which the biological tissue is in an initial tissue state and cell membranes of the biological tissue are substantially intact; a second stage in which the biological tissue is being heated and the cell membranes begin to rupture; a third stage in which the biological tissue is continued to be heated and the rupture of the cell membranes is substantially complete; a fourth stage in which the biological tissue is continued to be heated and a limited amount of tissue desiccation occurs, and moisture content of the biological tissue remains substantially near a peak moisture content, in liquid phase, with substantially minimal loss through vaporization; a fifth stage in which substantial tissue desiccation begins; a sixth stage in which tissue desiccation is substantially complete; and a seventh stage in which tissue desiccation is complete;

wherein the second stage is determined based on a decreasing value of real impedance and an increasing value of imaginary impedance; wherein the fourth stage is determined based on a minimum change in real impedance values and a minimum change in imaginary impedance values; wherein the fifth stage is determined based on a first increasing value of real impedance, and the imaginary impedance reaching a maximum value; and wherein the sixth stage is determined based on a second increasing value of real impedance and a decreasing value of imaginary impedance.

2. The system of claim 1, wherein the control circuitry is programmed or configured to determine the impedance measurement based on an average of the real impedance and the imaginary impedance.

3. The system of claim 1, wherein the control circuitry is programmed or configured to determine the impedance measurement based on a weighting of the real impedance that is different than a weighting of the imaginary impedance.

4. The system of claim 3, wherein the control circuitry is programmed or configured to determine the weighting of the real impedance and the weighting of the imaginary impedance dynamically based on an instantaneous impedance span of the impedance measurement at the plurality of frequencies.

5. The system of claim 3, wherein the control circuitry is programmed or configured to determine the weighting of the real impedance and the weighting of the imaginary impedance dynamically based on a rate of change of the impedance measurement at the plurality of frequencies over the plurality of time points.

6. The system of claim 1, wherein the control circuitry is programmed or configured to continuously receive or determine the impedance measurement of the biological tissue.

7. The system of claim 1, wherein the control circuitry is programmed or configured to periodically receive or determine the impedance measurement of the biological tissue.

8. The system of claim 1, wherein the control circuitry is programmed or configured to:

determine a rate of change of the impedance measurement of the biological tissue at the plurality of frequencies over the plurality of time points; and adjust or cause to be adjusted the power delivered to the biological tissue at the subsequent time point based on the rate of change of the impedance measurement of the biological tissue at the plurality of frequencies over the plurality of time points.

9. The system of claim 8, wherein the control circuitry is programmed or configured to:

receive or determine an average power delivered to the biological tissue at the plurality of frequencies over the plurality of time points; and adjust or cause to be adjusted the power delivered to the biological tissue at the subsequent time point based on the average power.

10. The system of claim 9, wherein the plurality of time points comprise a first time point and a second time point, and wherein the control circuitry is programmed or configured to:

determine a difference in the impedance measurement at the plurality of frequencies between the first time point and the second time point; and adjust or cause to be adjusted the power delivered to the biological tissue at the subsequent time point based on the difference in the impedance measurement at the plurality of frequencies between the first time point and the second time point.

11. The system of claim 1, wherein the control circuitry is programmed or configured to adjust or cause to be adjusted the power delivered to the biological tissue at the subsequent time point based on the following equation:

$$P_{t3} = ([P_{t1}+P_{t2}]/2) - k_A * [\Delta Z_{t2} - \Delta Z_{t1}]/[\Delta Z_{t2}+\Delta Z_{t1}] * ([P_{t1}+P_{t2}]/2)$$

wherein $P_{tn}$=power delivered to the biological tissue at time tn, $k_A$=scaling constant A where $0 \le k_A \le 1$, $\Delta Z_{tn}$=maximum $Z_{real}$-minimum $Z_{real}$, as measured at time tn, and time point t1 occurs before time point t2, which occurs before time point t3.

12. The system of claim 1, wherein the control circuitry is programmed or configured to adjust or cause to be adjusted the power delivered to the biological tissue at the subsequent time point based on the following equation:

$$P_{t3} = ([P_{t1}+P_{t2}]/2) - k_A * ([P_{t1}+P_{t2}]/2) * 0.5 * ([\Delta Z_{real@t2} - \Delta Z_{real@t1}]/[\Delta Z_{real@t2}+\Delta Z_{real@t1}] + ([\Delta Z_{imag@t2} - \Delta Z_{imag@t1}]/[\Delta Z_{imag@t2}+\Delta Z_{imag@t1}])$$

wherein $P_{tn}$=power delivered to the biological tissue at time tn, $k_A$=scaling constant A where $0 \le k_A \le 1$, time point t1 occurs before time point t2, which occurs before time point t3, $\Delta Z_{real@tn}$=maximum Zreal−minimum Zreal, as measured at time tn, and $\Delta Z_{imag@tn}$=maximum Zimag−minimum Zimag, as measured at time tn.

13. The system of claim 1, wherein the control circuitry is programmed or configured to adjust or cause to be adjusted the power delivered to the biological tissue at the subsequent time point based on the following equation:

$$P_{t3} = ([P_{t1} \, P_{t2}]/2) - k_r * ([P_{t1}+P_{t2}]/2) * [\Delta Z_{real@t2} - \Delta Z_{real@t1}]/[\Delta Z_{real@t2} - \Delta Z_{real@t1}] - k_i * ([P_{t1}-P_{t2}]/2) * [\Delta Z_{imag@t2} - \Delta Z_{imag@t1}]/[\Delta Z_{imag@t2} - \Delta Z_{imag@t1}]$$

wherein $k_r$ and $k_i$ are scaling constants for real and imaginary portions respectively, $P_{tn}$=power delivered to the biological tissue at time tn, time point t1 occurs before time point t2, which occurs before time point t3, $\Delta Z_{real@tn}$=maximum Zreal–minimum Zreal, as measured at time tn, and $\Delta Z_{imag@tn}$=maximum Zimag–minimum Zimag, as measured at time tn.

14. The system of claim 1, wherein the control circuitry is programmed or configured to:
  during the first weld stage, adjust or cause to be adjusted the power delivered to the biological tissue at the subsequent time point based on a first power adjustment algorithm; and
  during the second weld stage, adjust or cause to be adjusted the power delivered to the biological tissue at the subsequent time point based on a second power adjustment algorithm different than the first power adjustment algorithm.

15. The system of claim 14, wherein the first power adjustment algorithm is more sensitive to changes in the impedance measurement at the plurality of frequencies and the plurality of time points than the second power adjustment algorithm.

16. A biological tissue monitoring system comprising:
  control circuitry programmed or configured to monitor an impedance of biological tissue during electrosurgical welding of the biological tissue, wherein the control circuitry is programmed or configured to:
    receive or determine an impedance measurement of the biological tissue in response to a power delivered to the biological tissue at a plurality of frequencies and a plurality of time points, wherein the impedance measurement comprises real impedance and imaginary impedance;
    adjust or cause to be adjusted the power delivered to the biological tissue at a subsequent time point based on the impedance measurement at the plurality of frequencies and the plurality of time points;
    determine based on the impedance measurement at the plurality of frequencies and the plurality of time points a current weld stage of the biological tissue; and
    adjust or cause to be adjusted the power delivered to the biological tissue at the subsequent time point based on the current weld stage of the biological tissue;
    wherein the current weld stage includes a first stage in which the biological tissue is in an initial tissue state and cell membranes of the biological tissue are substantially intact; a second stage in which the biological tissue is being heated and the cell membranes begin to rupture; a third stage in which the biological tissue is continued to be heated and the rupture of the cell membranes is substantially complete; a fourth stage in which the biological tissue is continued to be heated and a limited amount of tissue desiccation occurs, and moisture content of the biological tissue remains substantially near a peak moisture content, in liquid phase, with substantially minimal loss through vaporization; a fifth stage in which substantial tissue desiccation begins; a sixth stage in which tissue desiccation is substantially complete; and a seventh stage in which tissue desiccation is complete;
    wherein the fourth stage is determined based on a minimum change in real impedance values and a minimum change in imaginary impedance values; and
    wherein the control circuitry is programmed or configured to deliver the power to the biological tissue at a decreased power level during the fourth stage based on the determination that the biological tissue is in the fourth stage in order to prolong the duration of the fourth stage.

17. The system of claim 16, wherein the second stage is determined based on a decreasing value of real impedance and an increasing value of imaginary impedance.

18. The system of claim 16, wherein the fifth stage is determined based on an increasing value of real impedance, and the imaginary impedance reaching a maximum value.

19. The system of claim 16, wherein the sixth stage is determined based on an increasing value of real impedance and a decreasing value of imaginary impedance.

20. A biological tissue monitoring system comprising:
  control circuitry programmed or configured to monitor an impedance of biological tissue during electrosurgical welding of the biological tissue, wherein the control circuitry is programmed or configured to:
    receive or determine an impedance measurement of the biological tissue in response to a power delivered to the biological tissue at a plurality of frequencies and a plurality of time points, wherein the impedance measurement comprises real impedance and imaginary impedance;
    adjust or cause to be adjusted the power delivered to the biological tissue at a subsequent time point based on the impedance measurement at the plurality of frequencies and the plurality of time points;
    determine based on the impedance measurement at the plurality of frequencies and the plurality of time points a current weld stage of the biological tissue; and
    adjust or cause to be adjusted the power delivered to the biological tissue at the subsequent time point based on the current weld stage of the biological tissue;
    wherein the current weld stage includes a first stage in which the biological tissue is in an initial tissue state and cell membranes of the biological tissue are substantially intact; a second stage in which the biological tissue is being heated and the cell membranes begin to rupture; a third stage in which the biological tissue is continued to be heated and the rupture of the cell membranes is substantially complete; a fourth stage in which the biological tissue is continued to be heated and a limited amount of tissue desiccation occurs, and moisture content of the biological tissue remains substantially near a peak moisture content, in liquid phase, with substantially minimal loss through vaporization; a fifth stage in which substantial tissue desiccation begins; a sixth stage in which tissue desiccation is substantially complete; and a seventh stage in which tissue desiccation is complete;
    wherein the control circuitry is programmed or configured to adjust or cause to be adjusted the power delivered to the biological tissue at the subsequent time point based on the following equation:
    if the real impedance has not reached a minimum value, then:

$$P_{t3} = 1.25 * ([P_{t1}+P_{t2}]/2) - k_A * [\Delta Z_{t2} - \Delta Z_{t1}]/[\Delta Z_{t2} + \Delta Z_{t1}] * ([P_{t1}+P_{t2}]/2);$$

otherwise, $$P_{t3} = ([P_{t1}+P_{t2}]/2) - k_A * [\Delta Z_{t2} - \Delta Z_{t1}]/[\Delta Z_{t2} + \Delta Z_{t1}] * ([P_{t1}+P_{t2}]/2)$$

wherein $P_{tn}$=power delivered to the biological tissue at time tn, $k_A$=scaling constant A where $0 \leq k_A \leq 1$, $\Delta Z_{tn}$=maximum $Z_{real}$–minimum $Z_{real}$, as measured at time tn, and time point t1 occurs before time point t2, which occurs before time point t3.

21. The system of claim 20, wherein the second stage is determined based on a decreasing value of real impedance and an increasing value of imaginary impedance; wherein the fourth stage is determined based on a minimum change in real impedance values and a minimum change in imaginary impedance values; wherein the fifth stage is determined based on a first increasing value of real impedance, and the imaginary impedance reaching a maximum value; and wherein the sixth stage is determined based on a second increasing value of real impedance and a decreasing value of imaginary impedance.

* * * * *